United States Patent
Oka

(10) Patent No.: US 10,602,041 B2
(45) Date of Patent: Mar. 24, 2020

(54) IMAGE CAPTURING DEVICE

(71) Applicant: OLYMPUS CORPORATION, Hachioji-shi, Tokyo (JP)

(72) Inventor: Tetsuhiro Oka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/156,828

(22) Filed: Oct. 10, 2018

(65) Prior Publication Data

US 2019/0082085 A1    Mar. 14, 2019

Related U.S. Application Data

(63) Continuation of application No. PCT/JP2016/061986, filed on Apr. 14, 2016.

(51) Int. Cl.
*H04N 5/225* (2006.01)
*G02B 23/24* (2006.01)
(Continued)

(52) U.S. Cl.
CPC ....... *H04N 5/2254* (2013.01); *A61B 1/00096* (2013.01); *A61B 1/0623* (2013.01);
(Continued)

(58) Field of Classification Search
None
See application file for complete search history.

(56) References Cited

U.S. PATENT DOCUMENTS

| 4,529,267 A | 7/1985 | Nishioka et al. |
| 6,334,688 B1 | 1/2002 | Niwa |

(Continued)

FOREIGN PATENT DOCUMENTS

| EP | 2815691 A1 | 12/2014 |
| EP | 2865318 A1 | 4/2015 |

(Continued)

OTHER PUBLICATIONS

International Search Report (ISR) dated Jun. 21, 2016 issued in International Application No. PCT/JP2016/061986.

(Continued)

*Primary Examiner* — James M Hannett
(74) *Attorney, Agent, or Firm* — Holtz, Holtz & Volek PC

(57) ABSTRACT

An image capturing device includes: an image capturing system having an optical axis; and at least one illumination system disposed at a position so as to surround the optical axis. The illumination system includes: a reflective surface deflecting part of illumination light; a refractive surface deflecting the other part of the illumination light and the illumination light reflected by the reflective surface; and an emission surface from which the illumination light refracted by the refractive surface is emitted. In a cross section including the optical axis, the reflective surface has an area inclined in such a direction as to become farther away from the optical axis, the refractive surface has an area inclined in such a direction as to approach the optical axis and is disposed between the reflective and emission surfaces. The emission end is disposed at a radial position between rear ends of the refractive and reflective surfaces.

10 Claims, 28 Drawing Sheets

(51) Int. Cl.
  *A61B 1/07*    (2006.01)
  *A61B 1/00*    (2006.01)
  *G02B 23/26*   (2006.01)
  *A61B 1/06*    (2006.01)
  *G02B 27/09*   (2006.01)

(52) U.S. Cl.
  CPC .............. *A61B 1/07* (2013.01); *G02B 23/243* (2013.01); *G02B 23/2469* (2013.01); *G02B 23/26* (2013.01); *G02B 27/0955* (2013.01); *G02B 27/0977* (2013.01); *H04N 5/2256* (2013.01); *H04N 5/22521* (2018.08); *H04N 2005/2255* (2013.01)

(56) References Cited

U.S. PATENT DOCUMENTS

| | | | |
|---|---|---|---|
| 2006/0067620 A1 | 3/2006 | Shishkov et al. | |
| 2012/0051693 A1 | 3/2012 | Yoshida et al. | |
| 2014/0346332 A1 | 11/2014 | Honda | |
| 2014/0347878 A1* | 11/2014 | Honda | ............... G02B 23/2461 362/574 |
| 2016/0103312 A1 | 4/2016 | Furuta | |
| 2017/0269348 A1* | 9/2017 | Shinji | ................... G02B 23/26 |

FOREIGN PATENT DOCUMENTS

| | | |
|---|---|---|
| EP | 3020321 A1 | 5/2016 |
| JP | 57097509 A | 6/1982 |
| JP | 10239596 A | 9/1998 |
| JP | 2000207916 A | 7/2000 |
| JP | 2003225202 A | 8/2003 |
| JP | 2012090723 A | 5/2012 |
| JP | 4997112 B2 | 8/2012 |
| JP | 5484263 B2 | 5/2014 |
| JP | 2015016021 A | 1/2015 |
| JP | 5663707 B2 | 2/2015 |
| WO | 2006037132 A1 | 4/2006 |
| WO | 2014073426 A1 | 5/2014 |

OTHER PUBLICATIONS

Written Opinion dated Jun. 21, 2016 issued in International Application No. PCT/JP2016/061986.

* cited by examiner

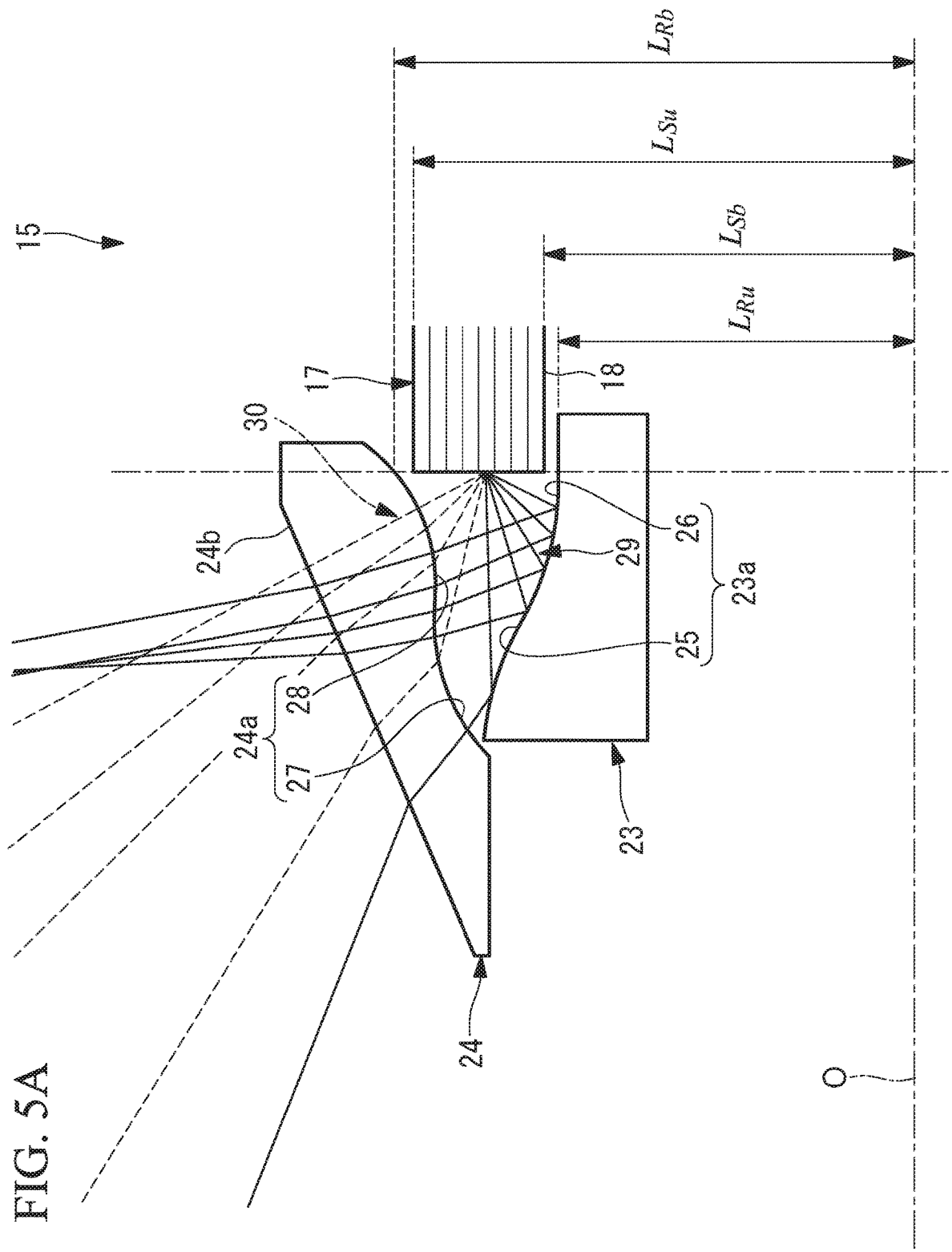

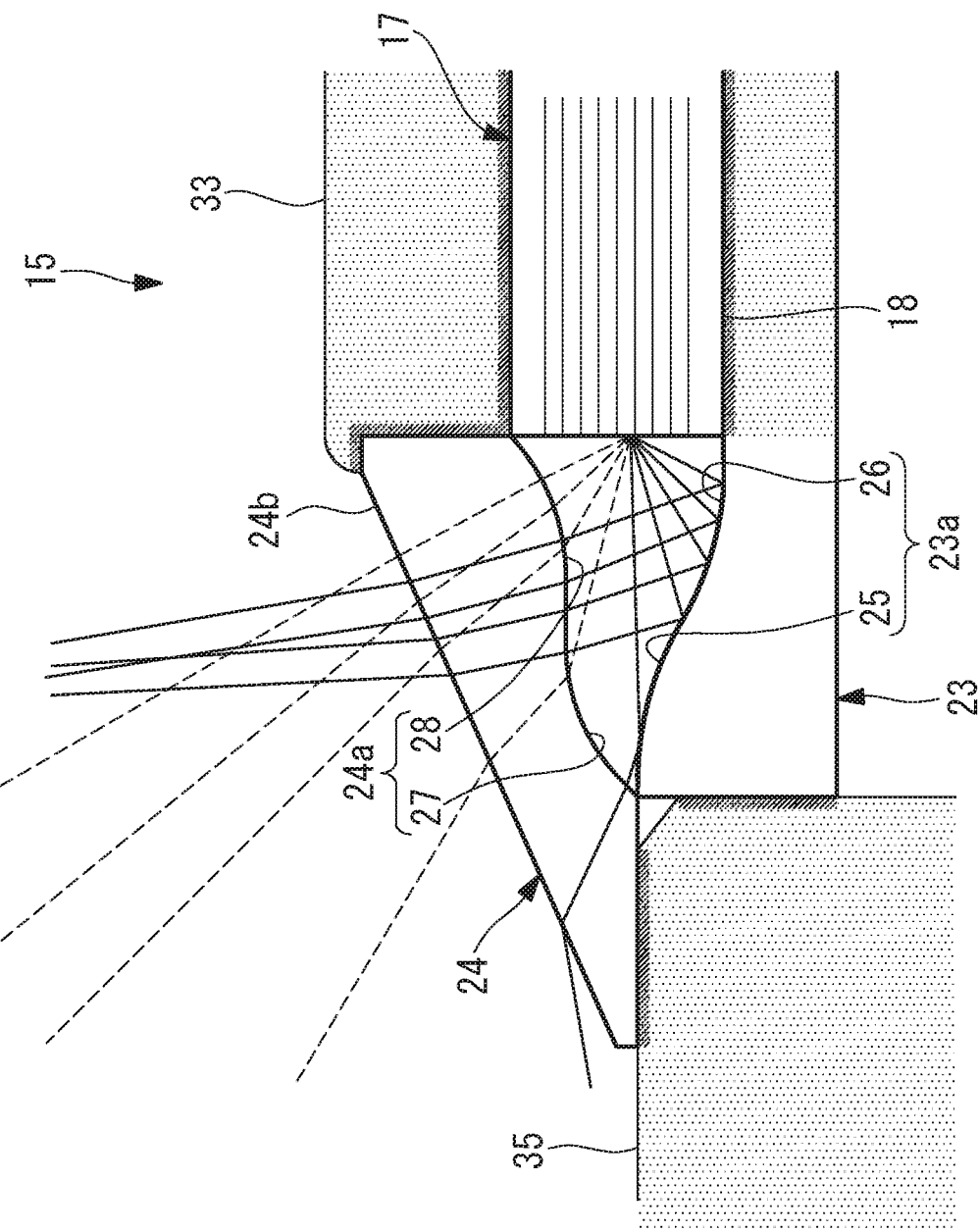

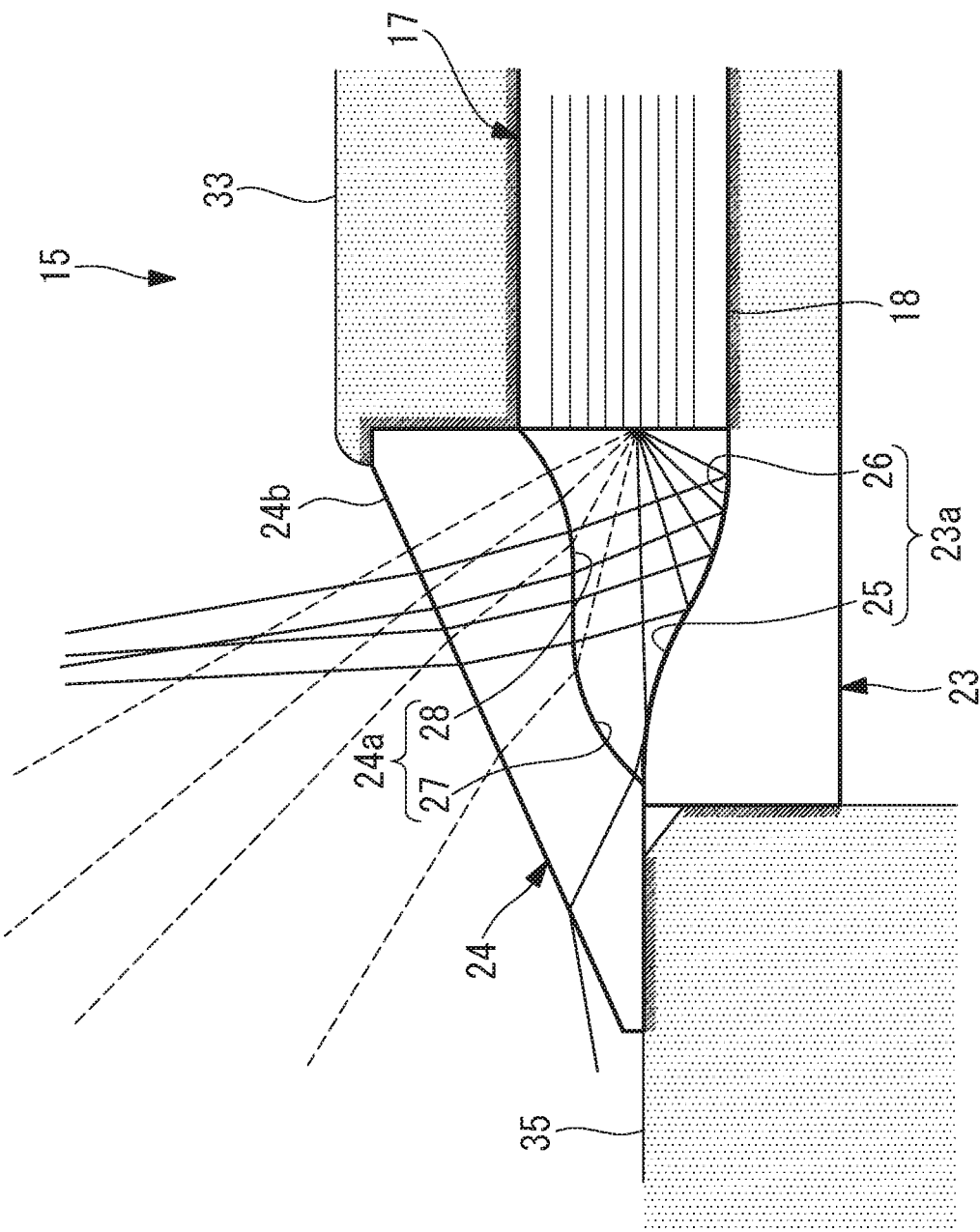

IMAGE CAPTURING DEVICE

CROSS-REFERENCE TO RELATED APPLICATIONS

This is a continuation of International Application PCT/JP2016/061986 which is hereby incorporated by reference herein in its entirety.

TECHNICAL FIELD

The present invention relates to an image capturing device.

BACKGROUND ART

There is a known endoscope that has a wide angle of view of 180° or more and that can simultaneously observe front, lateral, and rear fields of view (for example, see PTL 1). In the endoscope of PTL 1, for example, when the endoscope, which has an angle of view of 180° or more, is used in the large intestine, which has a number of folds, it is possible to observe the rear sides of the folds without significantly changing the direction of a distal end of the endoscope, thus facilitating the operation performed by a user, and to reliably find a lesion. An illumination device of this endoscope diffusely emits illumination light guided by a light guide, by using a diffusion layer, thereby making it possible to uniformly illuminate a wide range, including a lateral area and a forward area.

CITATION LIST

Patent Literature

{PTL 1} Japanese Unexamined Patent Application, Publication No. 2015-16021

SUMMARY OF INVENTION

According to one aspect, the present invention provides an image capturing device including: an image capturing optical system that has an optical axis and that captures an image of surroundings in directions around the optical axis; and at least one illumination optical system that is disposed at a position so as to surround the optical axis of the image capturing optical system, wherein the illumination optical system is provided with: a reflective surface that deflects, through reflection, part of illumination light emitted from an emission end from which the illumination light from a light source unit is emitted; a refractive surface that deflects, through refraction, the other part of the illumination light and the illumination light that has been reflected by the reflective surface; and an emission surface from which the illumination light that has been refracted by the refractive surface is emitted; in a cross section including the optical axis, the reflective surface has an area that is inclined in such a direction as to become farther away from the optical axis toward the front side; the refractive surface has an area that is inclined in such a direction as to approach the optical axis toward a front side and is disposed between the reflective surface and the emission surface; and the emission end is disposed at a radial position between a rear end of the refractive surface and a rear end of the reflective surface.

BRIEF DESCRIPTION OF DRAWINGS

FIG. 5A is a longitudinal sectional view showing an illumination optical system provided in the image capturing device shown in FIG. 1.

FIG. 13B is a longitudinal sectional view showing a state in which a first member and a second member of the illumination optical system shown in FIG. 13A are shifted in the axial direction.

FIG. 13C is a longitudinal sectional view showing a state in which the first member and the second member of the illumination optical system shown in FIG. 13A are further shifted in the axial direction.

DESCRIPTION OF EMBODIMENTS

An image capturing device 1 according to one embodiment of the present invention will be described below with reference to the drawings.

Figure 1:
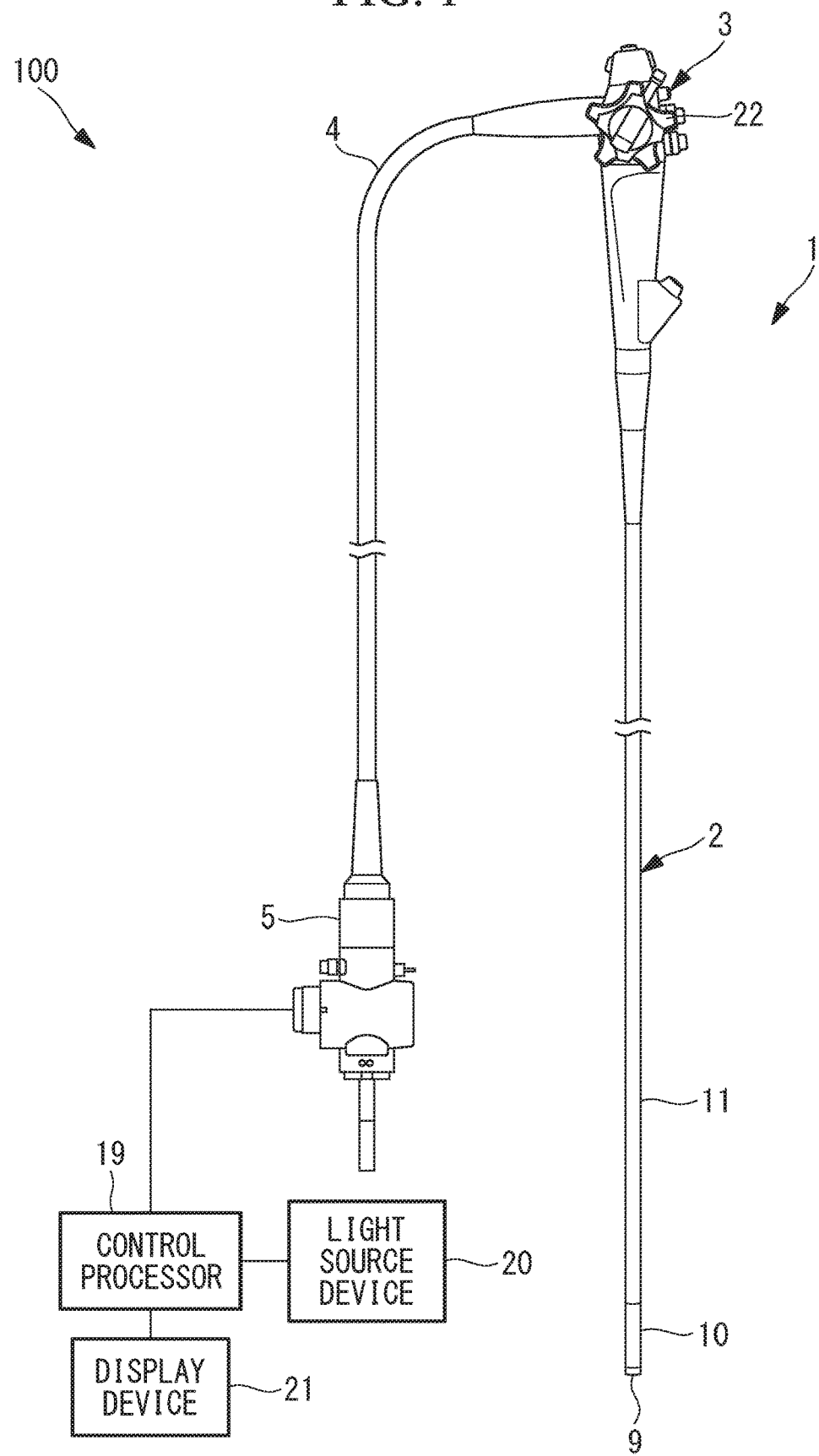
FIG. 1 is a view showing the overall configuration of an endoscope that serves as an example of an image capturing device according to one embodiment of the present invention.

As shown in FIG. 1, the image capturing device 1 of this embodiment is an endoscope and is provided with: an elongated insertion portion 2 that is inserted into a body cavity or the like; an operating part 3 that is provided at a proximal end of the insertion portion 2; a universal cord 4 that extends from the operating part 3; and a connector part 5 that is provided at a terminal end of the universal cord 4.

Figure 2:
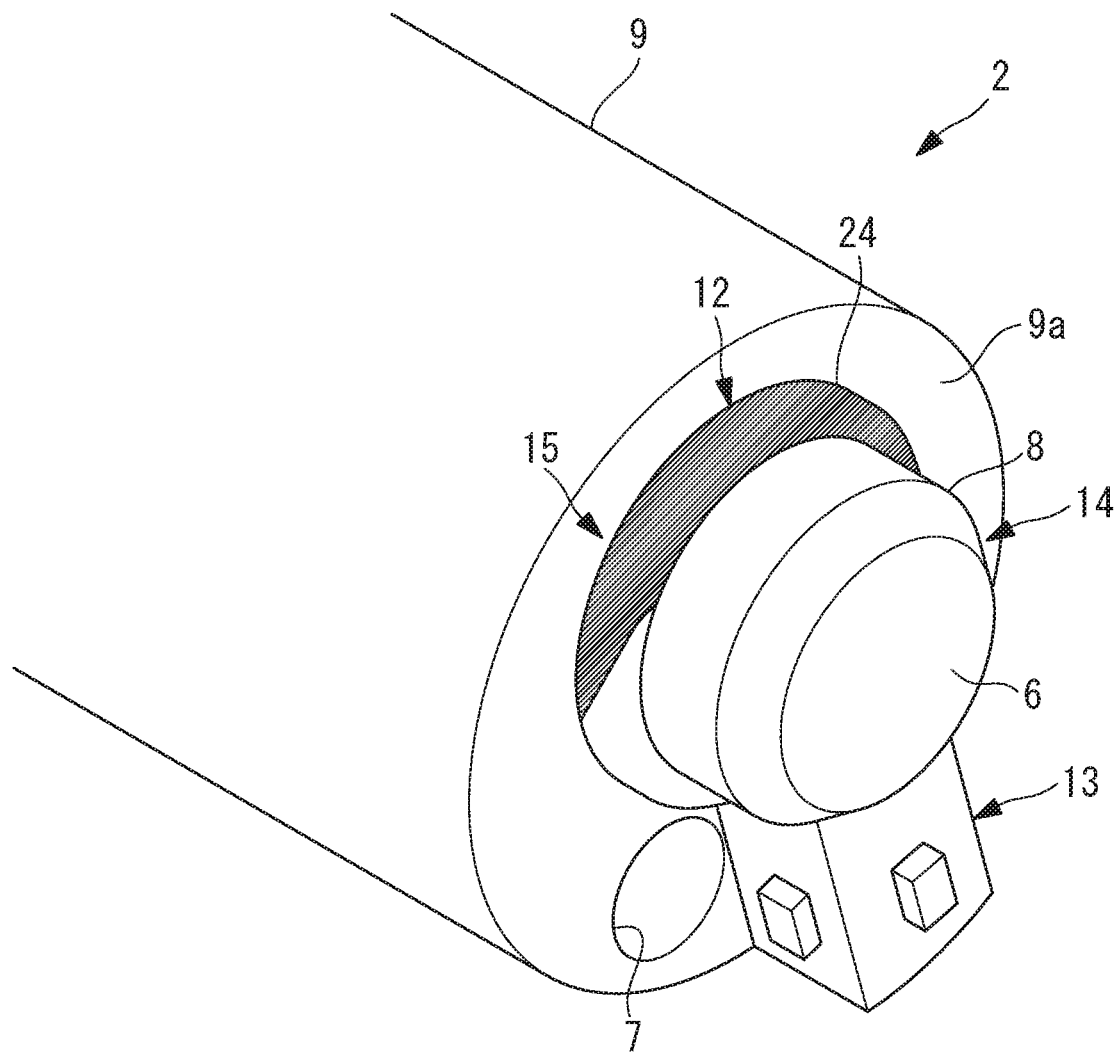
FIG. 2 is a perspective view showing a part of a distal end portion of the image capturing device shown in FIG. 1, in an enlarged manner.
Figure 3:
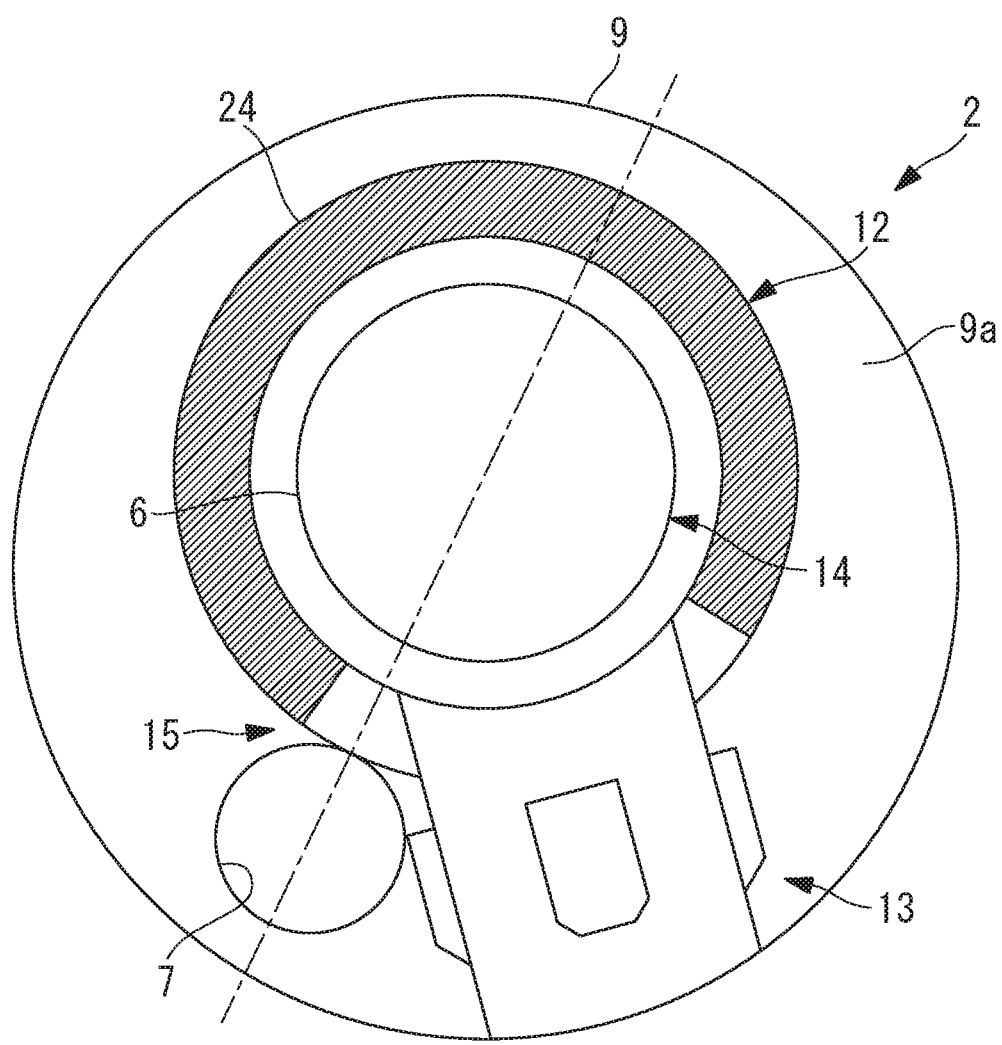
FIG. 3 is a front view showing the distal end portion of the image capturing device shown in FIG. 2.
Figure 4:
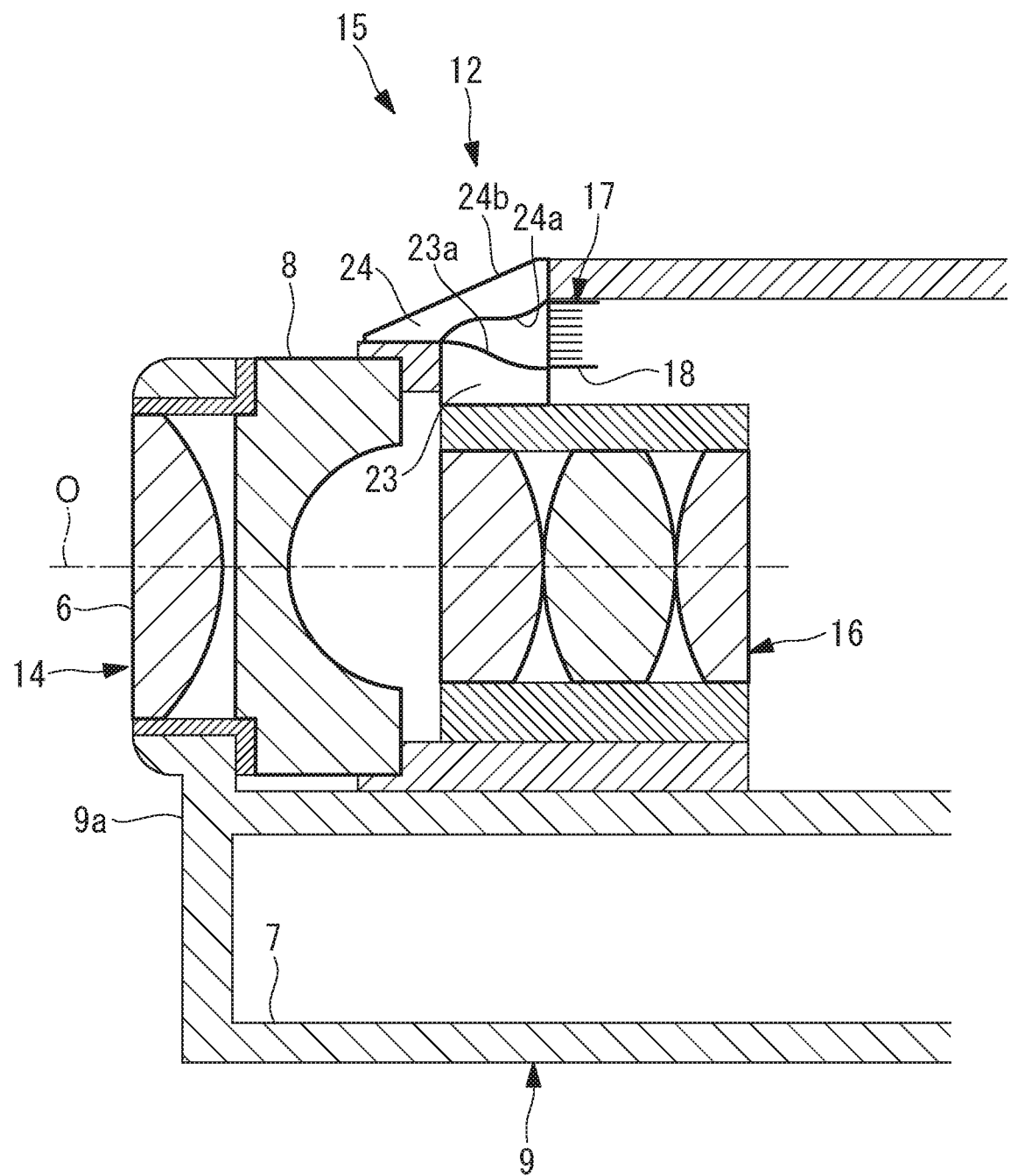
FIG. 4 is a partial, longitudinal sectional view showing the distal end portion of the image capturing device shown in FIG. 2.

At a distal end of the insertion portion 2, as shown in FIGS. 2 to 4, a direct-viewing forward-observation objective lens 6 is disposed on a distal-end surface 9a so as to be directed to the front side, and a side-viewing lateral-observation objective lens 8 and an illumination lens 12 are disposed in the vicinity of the forward-observation objective lens 6. Accordingly, the image capturing device 1 of this embodiment has a wide field-of-view range in which a front visual field and a lateral visual field can be simultaneously observed.

The forward-observation objective lens 6 images an observation target located at the front side of the insertion portion 2. Furthermore, the lateral-observation objective lens 8 is formed into a substantially cylindrical shape so as to image an observation target located at a lateral side of the insertion portion 2. The lateral-observation objective lens 8 is disposed closer to the proximal end of the insertion portion 2 than the forward-observation objective lens 6 is.

The insertion portion 2 is provided with: a rigid distal-end section 9 that is provided at a leading-end section thereof; a bending section 10 that is connected to the proximal end of the distal-end section 9; and a flexible tube section 11 that is connected to the proximal end of the bending section 10 and that is formed of a long tubular member having flexibility.

As shown in FIGS. 2 and 3, a treatment-tool channel opening 7, the forward-observation objective lens 6, the illumination lens 12, a water supply nozzle 13, etc., are disposed on the distal-end surface 9a of the distal-end section 9.

As shown in FIG. 4, an image capturing optical system 14 and an illumination optical system 15 are disposed inside the distal-end section 9 of the insertion portion 2. The image capturing optical system 14 is provided with: the forward-observation objective lens 6, which is exposed on the distal-end surface 9a; the lateral-observation objective lens 8, which is exposed on the side surface around the distal-end surface 9a; an imaging optical system 16 that is accommodated in the distal-end section 9; and an image acquisition element (not shown) that acquires an image of an observation target imaged by the imaging optical system 16.

A treatment-tool channel, a light guide 17, a signal cable (not shown), and the like are disposed in the insertion portion 2. The treatment-tool channel penetrates through the insertion portion 2 in the longitudinal direction from the treatment-tool channel opening 7 on the distal-end surface 9a and extends to a treatment-tool insertion port that is disposed in the vicinity of a connecting part between the insertion portion 2 and the operating part 3. Furthermore, the light guide 17 and the signal cable penetrate through the insertion portion 2 in the longitudinal direction from the distal-end section 9 of the insertion portion 2, pass through the inside of the universal cord 4 via the operating part 3, and are finally connected to the connector part 5 at the terminal end of the universal cord 4.

The light guide 17 is constituted of a fiber bundle of a plurality of light-guide fibers 18 used for guiding illumination light.

A control processor 19, a light source device (light source unit) 20, and a display device 21, which are external devices, are connected to the image capturing device 1 via the connector part 5, thereby constituting an endoscope system 100.

The operating part 3 is a part gripped by a user when the user uses the endoscope 1, and a bending operation knob 22 and other operation members for performing various types of operations are disposed on an exterior surface thereof. Here, for example, the bending operation knob 22 is an operation member that is rotationally operated by the user using his/her hand, fingers etc., thereby bending the bending section 10 of the insertion portion 2 in any direction, i.e., up and down, and left and right.

The light source device 20 is a device that produces illumination light. The control processor 19 is a signal processing device that comprehensively controls the overall endoscope system 100. The display device 21 is a display unit that displays an endoscopic image on the basis of an image-acquisition signal acquired by the endoscope 1, and is constituted of an LCD panel etc., for example.

The control processor 19 transmits a control signal, various types of detection signals, an acquired image signal, etc., via the signal cable inserted through the endoscope 1. Then, the control processor 19 transmits processed image signals to the display device 21 and causes an endoscopic image, various types of information, etc., to be displayed thereon. Furthermore, illumination light from the light source device 20 is guided to the illumination optical system 15, which is disposed in the insertion portion 2, via the connector part 5, the universal cord 4, and the operating part 3 and is radiated toward surrounding observation targets.

Figure 5B:
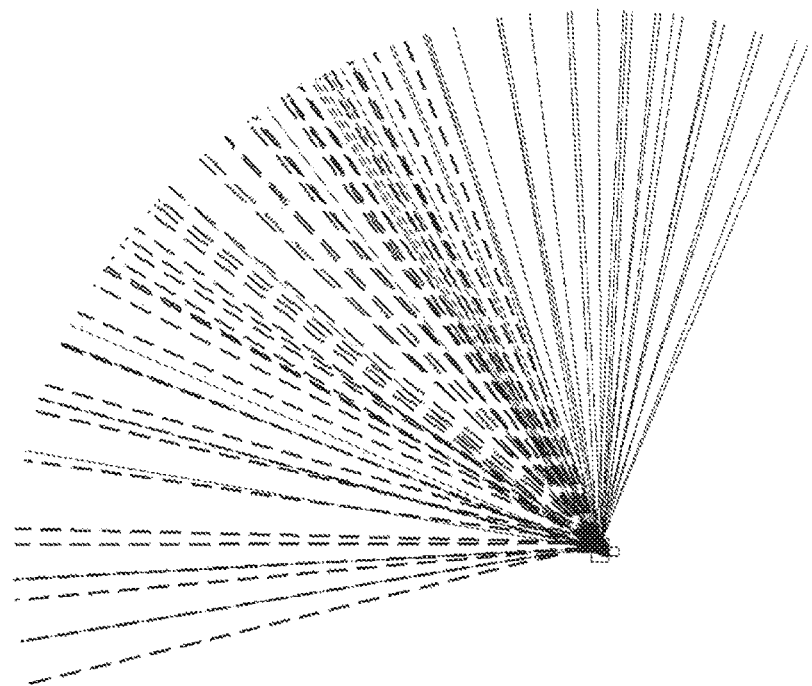
FIG. 5B is a reduced view showing an emission range in which illumination light is emitted by the illumination optical system shown in FIG. 5A.

As shown in FIGS. 5A and 5B, the illumination optical system 15 is provided with a first member 23 and a second member 24 that are coaxially disposed, at a radially outer side of the image capturing optical system 14, so as to surround the image capturing optical system 14 over a predetermined circumferential range centered on the optical axis O of the image capturing optical system 14. Air fills the space between the first member 23 and the second member 24.

The first member 23 is disposed at a radially inner side of the second member 24 and has a reflective surface 23*a* that deflects, through reflection, part of the illumination light that has been guided in the insertion portion 2 by the light guide 17 and that has been emitted from an emission end of the light guide 17.

As shown in FIG. 5A, in a longitudinal section including the optical axis O of the image capturing optical system 14, the reflective surface 23*a* has an area that is inclined in such a direction as to gradually become farther away from the optical axis O toward the front side in the traveling direction of the illumination light, and is provided with: a convex surface section (convex section) 25 that is convex toward the radially outer side; and a concave surface section (concave section) 26 that is disposed beside the convex surface section 25, at the rear side thereof in the direction of the optical axis O. A rear end of the reflective surface 23*a* of the first member 23 is disposed closer to the radially inner side than the emission end of the light guide 17 is, and a front end thereof is disposed almost at a radially center position in the radial range of the emission end of the light guide 17.

The second member 24 is provided with: a refractive surface 24*a* that receives illumination light reflected by the reflective surface 23*a* and the remaining illumination light from the emission end and that deflects the illumination light through refraction; and an emission surface 24*b* that emits, around the circumference thereof, the illumination light that has been refracted by the refractive surface 24*a*.

As shown in FIG. 5A, in a longitudinal section including the optical axis O of the image capturing optical system 14, the refractive surface 24*a* has an area that is inclined in such a direction as to gradually approach the optical axis O toward the front side in the traveling direction of the illumination light, and is provided with: a concave surface section (concave section, bent section) 27 that is convex toward the radially outer side; and a convex surface section (convex section, bent section) 28 that is disposed beside the concave surface section 27, at the rear side thereof in the direction of the optical axis O. A rear end of the refractive surface 24*a* of the second member 24 is disposed closer to the radially outer side than the emission end of the light guide 17 is, and a front end thereof is disposed almost at a radially center position in the radial range of the emission end of the light guide 17.

Specifically, in this embodiment, the illumination optical system 15 satisfies the following Conditional Expressions (1) and (2).

$$LRu \leq LSb \quad (1)$$

$$LSu \leq LRb \quad (2)$$

where, in FIGS. 5A and 5B,

LRu indicates the distance from the optical axis O to the intersection point of an extended line of the emission end of the light guide 17 in the radial direction and the reflective surface 23*a*, LSb indicates the distance from the optical axis O to the innermost position of the emission end of the light guide 17 in the radial direction, LSu indicates the distance from the optical axis O to the outermost position of the emission end of the light guide 17 in the radial direction, and LRb indicates the distance from the optical axis O to the intersection point of the extended line of the emission end of the light guide 17 in the radial direction and the refractive surface 24*a*.

Furthermore, in the illumination optical system 15, the reflective surface 23*a* is formed such that the intersection points of the normals of the reflective surface 23*a* in the area where the illumination light is incident and the extended line of the emission end of the light guide 17 in the radial direction are located at radially outer positions.

The operation of the thus-configured image capturing device 1 of this embodiment will be described below.

According to the image capturing device 1 of this embodiment, when illumination light guided by the light guide 17 is emitted from the emission end of the light guide 17, part of the illumination light that is emitted toward the radially inner side is mainly incident on the reflective surface 23*a*, and the rest of the illumination light that is emitted toward the radially outer side is incident on the refractive surface 24*a*.

As indicated by solid lines in FIGS. 5A and 5B, the illumination light incident on the reflective surface 23*a* is reflected by the reflective surface 23*a*, thus being deflected, is incident on the refractive surface 24*a*, thus being deflected again through refraction, and is deflected once again through refraction when emitted from the emission surface 24*b*, thus being emitted mainly to a lateral side of the image capturing device 1.

On the other hand, as indicated by broken lines in FIGS. 5A and 5B, the illumination light incident on the refractive surface 24*a* without being routed via the reflective surface 23*a* is deflected through refraction at the refractive surface 24*a* and is then deflected again through refraction when emitted from the emission surface 24*b*, thus being emitted mainly to the front side of the image capturing device 1.

Because the reflective surface 23*a* is provided with the convex surface section 25 at a position distant from the emission end of the light guide 17 in the axial direction, illumination light emitted from the emission end of the light guide 17 at a relatively shallow angle can be made incident on the convex surface section 25 and can be spread over a wide angular range extending up to a rear-side area. Accordingly, there is an advantage in that it is possible to secure a wide illuminated area and to capture an image of observation targets existing in the wide range.

Furthermore, because the reflective surface 23*a* is provided with the concave surface section 26, at the rear side of the convex surface section 25, adjacently thereto, illumination light incident on the concave surface section 26 can be prevented from returning toward the emission end of the light guide 17.

Then, because the reflective surface 23*a* is formed such that the intersection points of the normals of the reflective surface 23*a* in the area where the illumination light is incident and the extended line of the emission end of the light guide 17 in the radial direction are located at radially outer positions, the illumination light reflected at the reflective surface 23*a* is prevented from returning to the emission end of the light guide 17, thus making it possible to improve the illumination efficiency.

FIG. 5B simply shows an illuminated area illuminated with illumination light indicated by the solid lines and the broken lines shown in FIG. 5A, by reducing the scale of FIG. 5A. From FIG. 5B, it is found that illumination light indicated by the broken lines mainly illuminates a forward area, and illumination light indicated by the solid lines mainly illuminates a lateral area. Thus, illumination light emitted from the light guide 17 is branched into two groups so as to illuminate the lateral area and the forward area in this way, thereby making it possible to illuminate a wide-range area.

Furthermore, according to the image capturing device 1 of this embodiment, there is an advantage in that the boundary between the illumination light for illuminating the above-described lateral area and the illumination light for illuminating the above-described forward area can be eliminated due to refraction at the refractive surface 24*a*, which is disposed between the reflective surface 23*a* and the emission surface 24*b*, thus making it possible to perform uniform illumination. Because the refractive surface 24*a* also has the effect of refracting illumination light so as to make the illumination light incident on the emission surface 24*b* at angles at which total reflection does not occur, it is possible to suppress total reflection at the emission surface 24*b*, to prevent the occurrence of unwanted light, such as return light returning to the light guide 17, and to improve the illumination efficiency.

Furthermore, according to the image capturing device 1 of this embodiment, because the above-described Conditional Expressions (1) and (2) are satisfied, illumination light emitted from the emission end of the light guide 17 can be efficiently made to enter the illumination optical system 15.

Furthermore, an air space is provided between the reflective surface 23*a* and the refractive surface 24*a*, thereby making it possible to increase the refraction at the refractive surface 24*a*.

Furthermore, the refractive surface 24*a* is provided with the convex surface section 28 at the rear side thereof, thereby making it possible to dispose the refractive surface 24*a* in a state in which the refractive surface 24*a* is open toward the emission end of the light guide 17 and preventing illumination light passing through a section indicated by reference sign 29 in FIG. 5A from being refracted much. Accordingly, it is possible to minimize the percentage of overlapping with illumination light reflected at the reflective surface 23*a* and incident on the same area.

On the other hand, with the refractive surface 24*a* being provided with the concave surface section 27 at the front side thereof, illumination light passing through a section indicated by reference sign 30 in FIG. 5A can be refracted in directions away from the optical axis O or can be made incident on the emission surface 24*b* without being refracted, thereby making it possible to illuminate the forward area more.

Note that, in this embodiment, some of the normals of the reflective surface 23*a* may intersect with the emission end of the light guide 17. Specifically, 70% or more of illumination light reflected at the reflective surface 23*a* may be transmitted through the refractive surface 24*a* and may be emitted from the emission surface 24*b*.

Furthermore, a diffuser plate that diffuses illumination light may be disposed at a subsequent stage of the emission end of the light guide 17. Unevenness, such as color unevenness, of illumination light emitted from the emission end of the light guide 17 can be eliminated through diffusion at the diffuser plate.

Figure 6A:
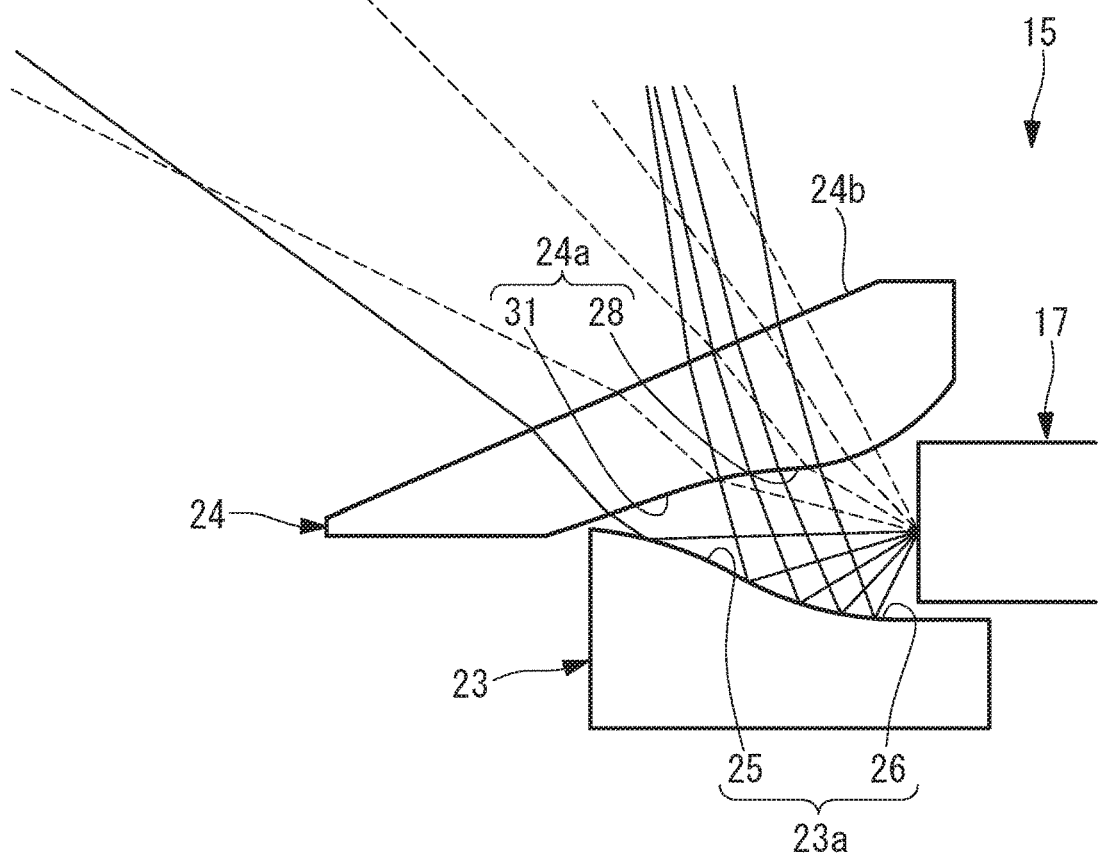
FIG. 6A is a longitudinal sectional view showing a first modification of the illumination optical system shown in FIG. 5A.
Figure 6B:
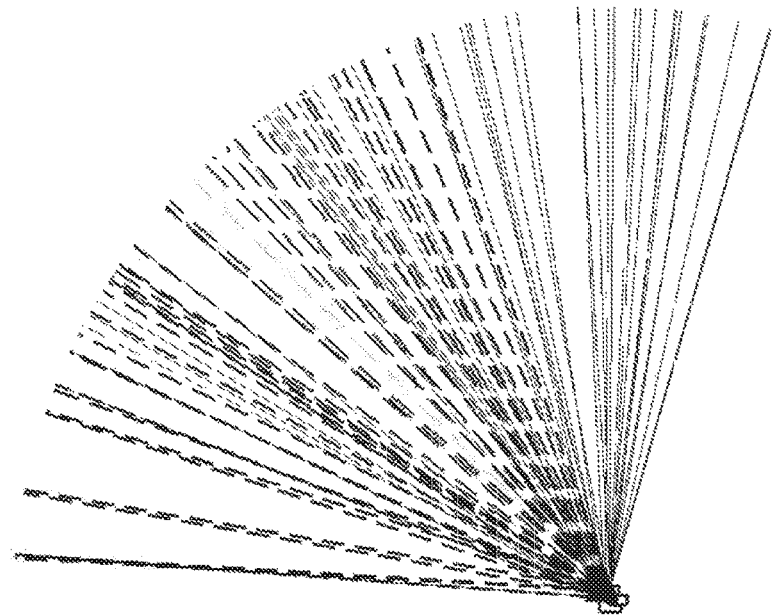
FIG. 6B is a reduced view showing an emission range in which illumination light is emitted by an illumination optical system shown in FIG. 6A.

Furthermore, as shown in FIG. 6A, the refractive surface 24*a* may be formed into a shape that has a linear flat section 31 at the front side thereof, in a longitudinal section including the optical axis O. The flat section 31 is adopted instead of the concave surface section 27, thereby making it possible to more laterally deflect illumination light that passes through this area. This is effective in limiting illumination with respect to the forward area. FIG. 6B shows an illumination range obtained by the illumination optical system 15 shown in FIG. 6A. As in FIG. 5B, the broken lines indicate illumination light that has not been routed via the reflective surface 23*a*, and the solid lines indicate illumination light that has been routed via the reflective surface 23*a*.

Figure 7A:
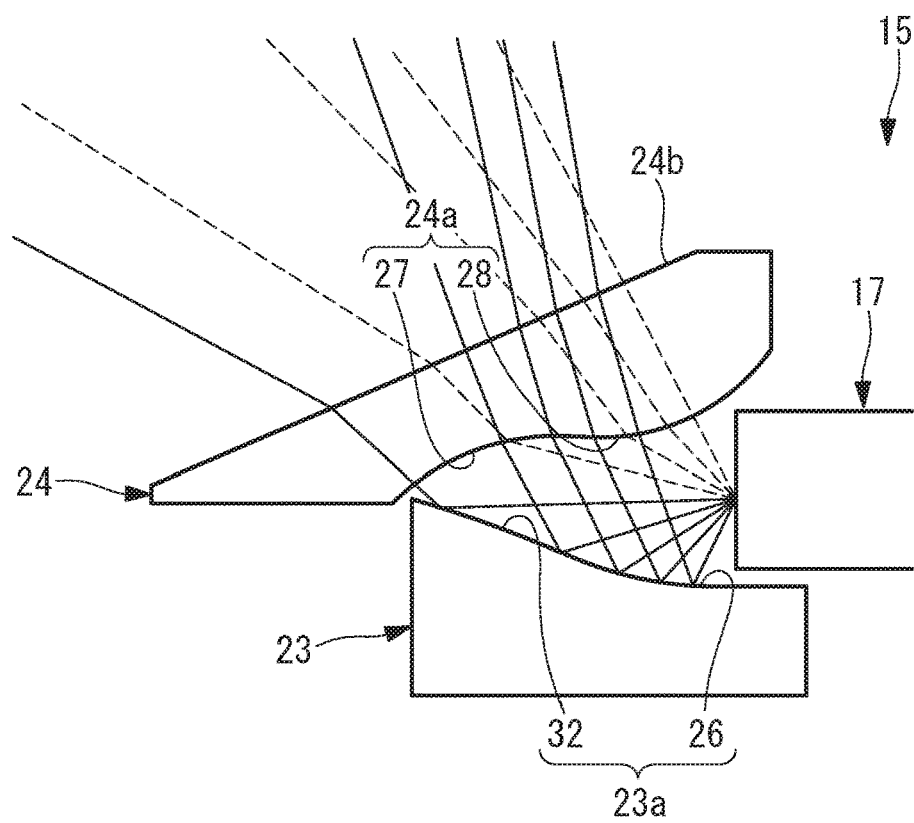
FIG. 7A is a longitudinal sectional view showing a second modification of the illumination optical system shown in FIG. 5A.
Figure 7B:
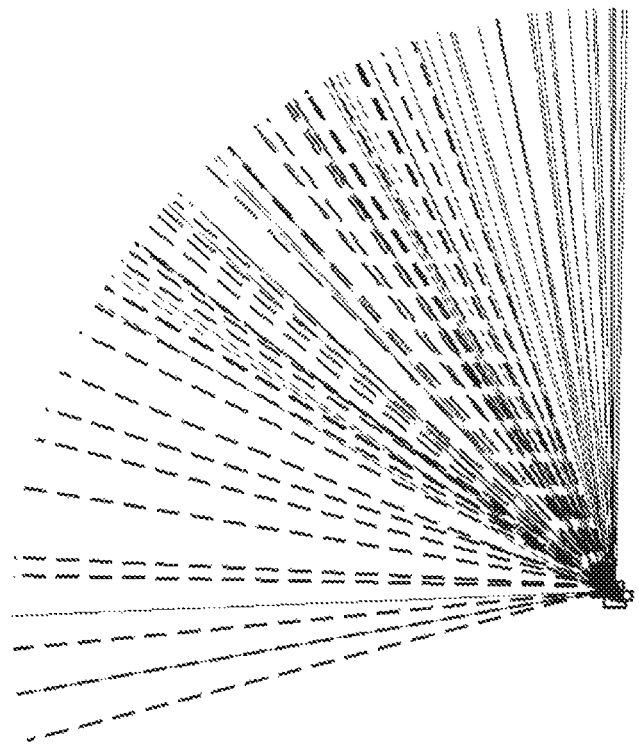
FIG. 7B is a reduced view showing an emission range in which illumination light is emitted by an illumination optical system shown in FIG. 7A.

Furthermore, as shown in FIG. 7A, the reflective surface 23*a* may be formed into a shape that has a linear flat section 32 at the front side thereof, in a longitudinal section including the optical axis O. The flat section 32 is adopted instead of the convex surface section 25, thereby making it possible to reduce the percentage of illumination light emitted toward the rear side. This is effective when illumination of a rear-side area is not necessary. FIG. 7B shows an illumination range obtained by the illumination optical system 15 shown in FIG. 7A. As in FIG. 5B, the broken lines indicate illumination light that has not been routed via the reflective surface 23*a*, and the solid lines indicate illumination light that has been routed via the reflective surface 23*a*.

Figure 8:
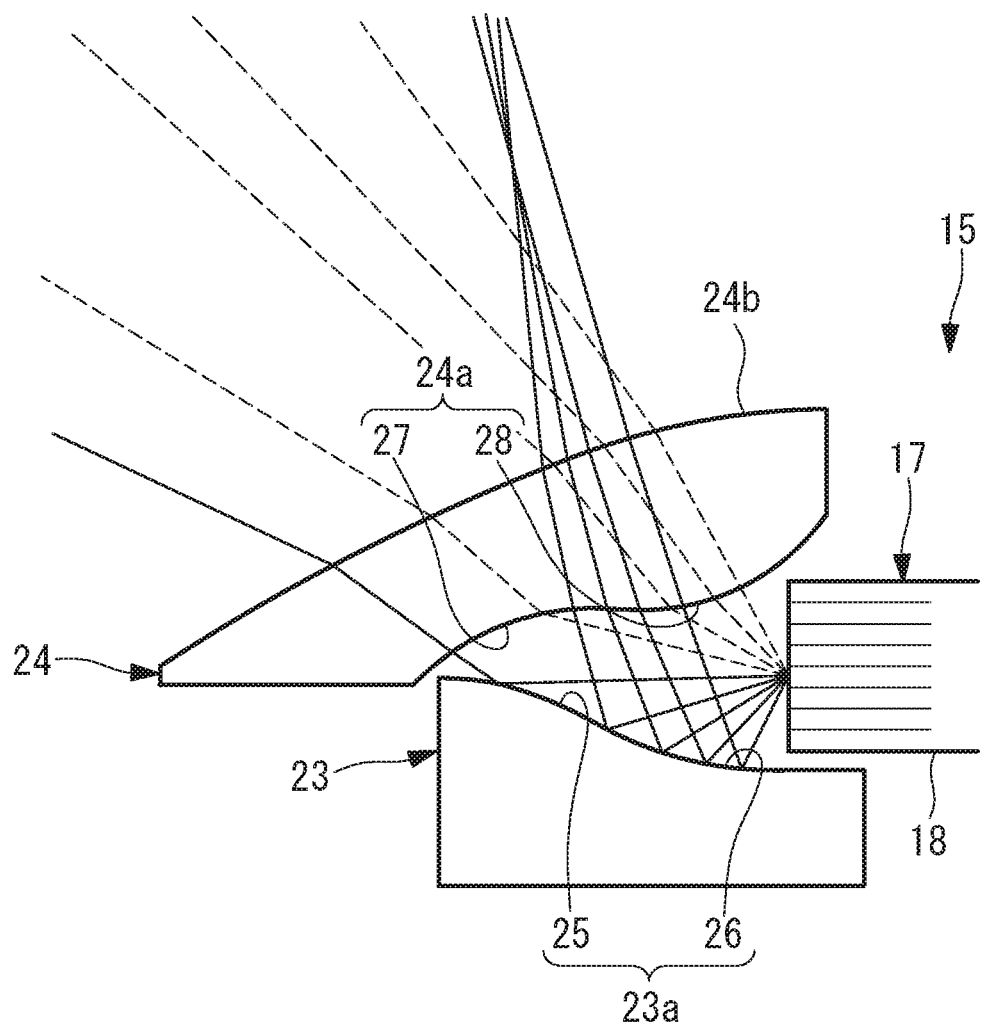
FIG. 8 is a longitudinal sectional view showing a third modification of the illumination optical system shown in FIG. 5A.

Furthermore, as shown in FIG. 8, the emission surface 24*b* may have a curved shape that is convex outward.

Figure 9A:
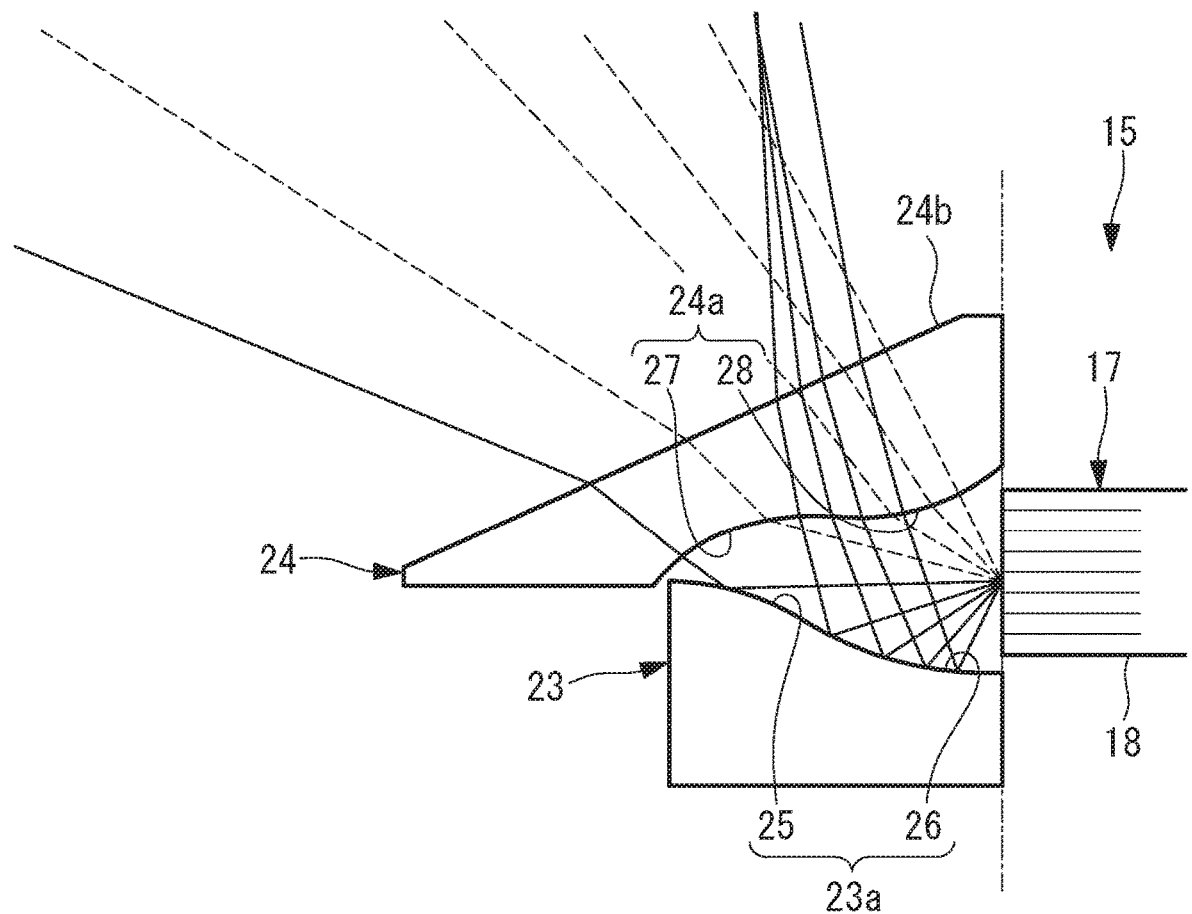
FIG. 9A is a longitudinal sectional view showing a fourth modification of the illumination optical system shown in FIG. 5A.
Figure 9B:
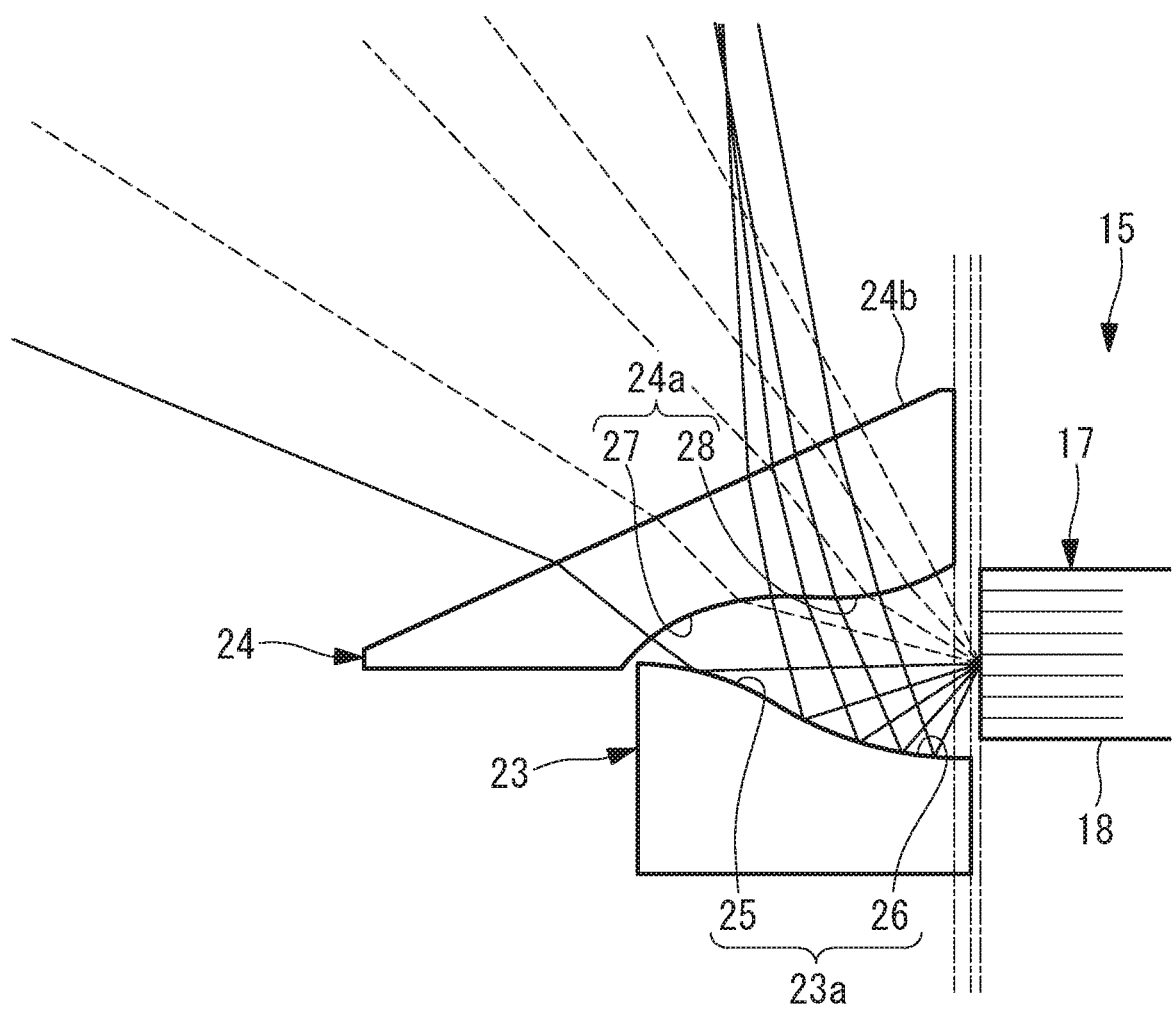
FIG. 9B is a longitudinal sectional view showing a modification of the positions of rear ends of a first member and a second member in an illumination optical system shown in FIG. 9A.

Furthermore, as shown in FIGS. 9A and 9B, the emission end of the light guide 17 and the rear ends of the first member 23 and the second member 24 may be aligned or may not be aligned in the direction of the optical axis O. The positional relationship between the first member 23, the second member 24, and the emission end of the light guide 17 can be freely determined according to a fixing method.

Figure 10:
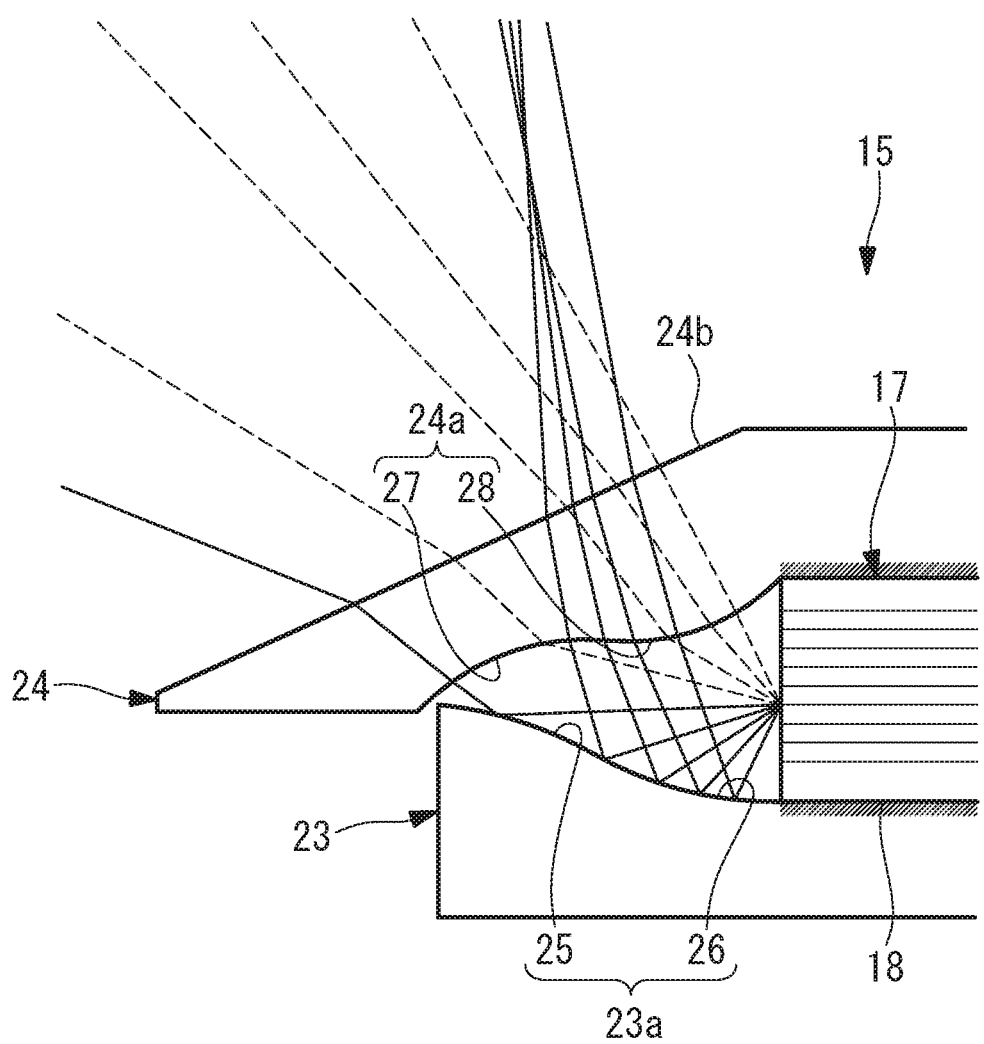
FIG. 10 is a longitudinal sectional view showing a fifth modification of the illumination optical system shown in FIG. 5A.
Figure 11:
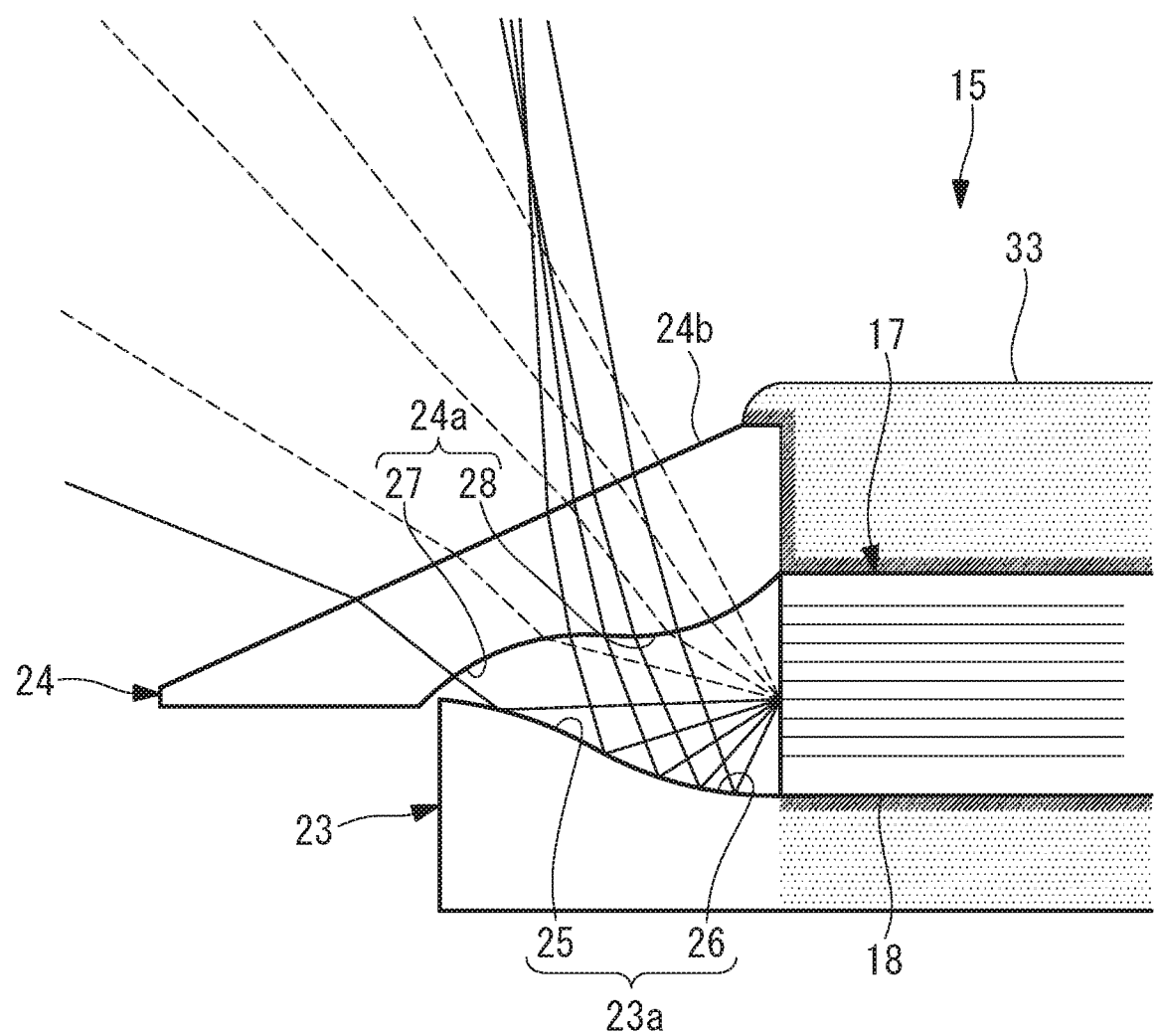
FIG. 11 is a longitudinal sectional view showing a fixing method with respect to a frame according to a sixth modification of the illumination optical system shown in FIG. 5A.

Furthermore, FIGS. 10 and 11 show example fixing methods for the light guide 17 and the illumination optical system 15.

FIG. 10 shows the fixing method in which the light guide 17 is radially sandwiched by the first member 23 and the second member 24 and is fixed thereto with an adhesive agent. Because illumination light does not pass through the side surfaces of the light guide 17, the adhesive agent to be used may be transparent or opaque. By doing so, watertightness of the air space formed between the reflective surface 23*a* and the refractive surface 24*a* can be easily achieved.

FIG. 11 shows the fixing method in which the light guide 17 is radially sandwiched between the first member 23 and a frame 33 and is bonded thereto, and the second member 24 is bonded to the frame 33 in the axial direction, thereby fixing the light guide 17 and the illumination optical system 15. An adhesive agent to be used may be transparent or opaque. With this method, the watertightness of the air space, which is formed between the reflective surface 23*a* and the refractive surface 24*a*, can also be easily achieved.

Figure 12A:
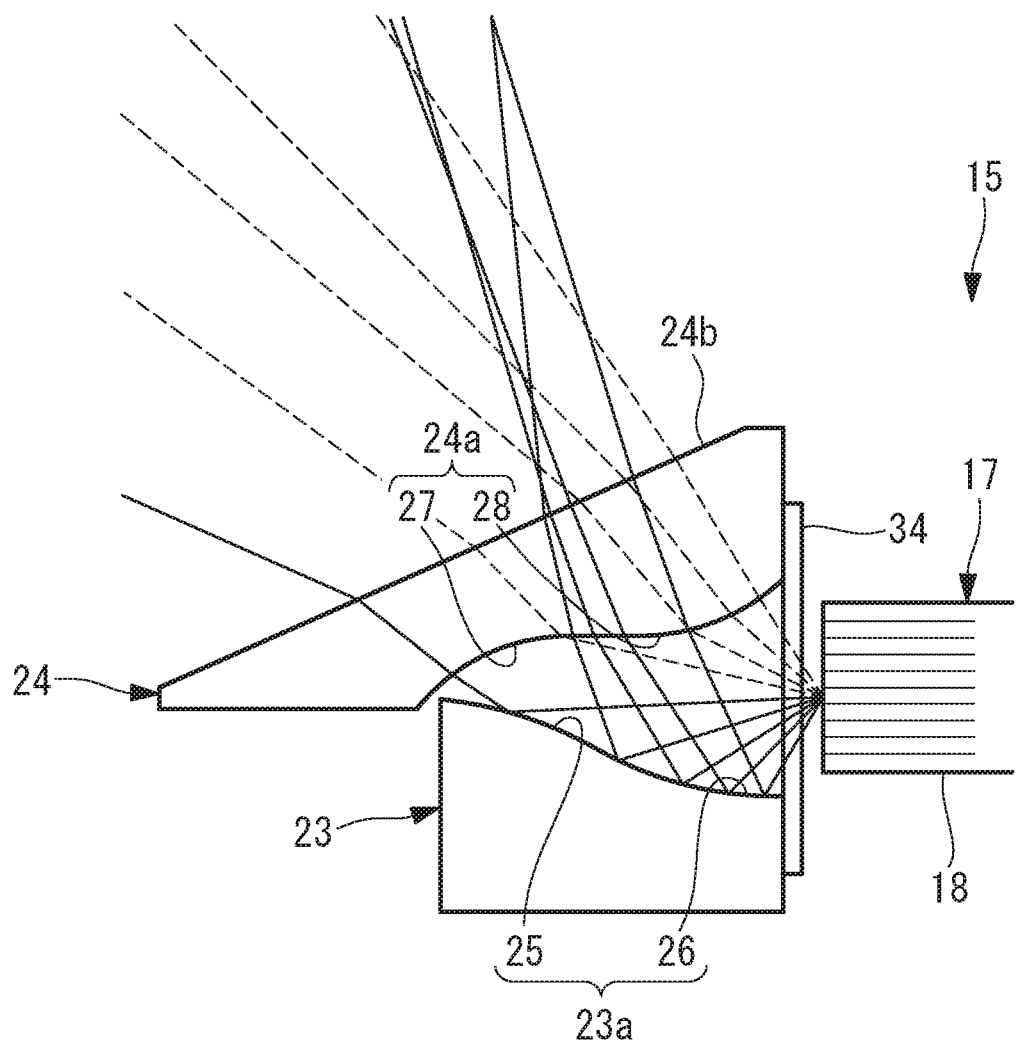
FIG. 12A is a longitudinal sectional view showing an illumination optical system that is provided with a sealing member, according to a seventh modification of the illumination optical system shown in FIG. 5A.

Furthermore, as shown in FIG. 12A, a gap between the members 23 and 24 may be sealed by a transparent tabular sealing member 34, on the rear end surfaces of the first member 23 and the second member 24. The emission end of the light guide 17 is disposed in close contact with or in the vicinity of the sealing member 34, and emitted illumination light is transmitted through the sealing member 34 and is made to enter the air space between the first member 23 and the second member 24.

Figure 12B:
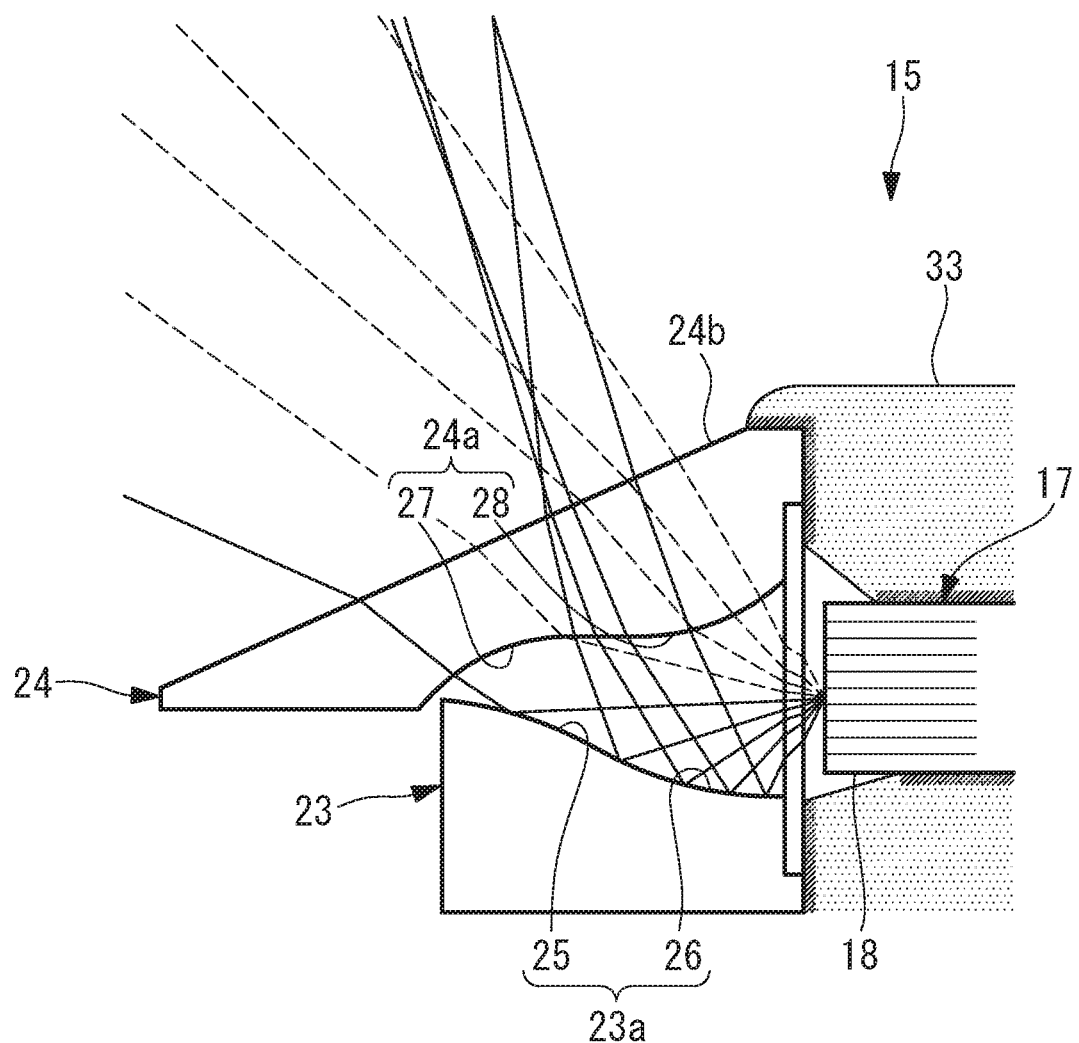
FIG. 12B is a longitudinal sectional view for explaining a fixing method of fixing the illumination optical system shown in FIG. 12A to the frame.

Furthermore, when fixing the light guide 17 and the illumination optical system 15 by using a frame 33, as shown in FIG. 12B, the frame 33 is bonded thereto. Furthermore, the sealing member 34 may be formed of a diffuser plate. There is an advantage in that the NA of illumination light emitted from the emission end of the light guide 17 can be increased, and the illumination light can be made to enter the air space, thus making it possible to expand the illumination range. Furthermore, there is also an effect of being able to eliminate unevenness, such as color unevenness, of illumination light emitted from the light guide 17.

Figure 13A:
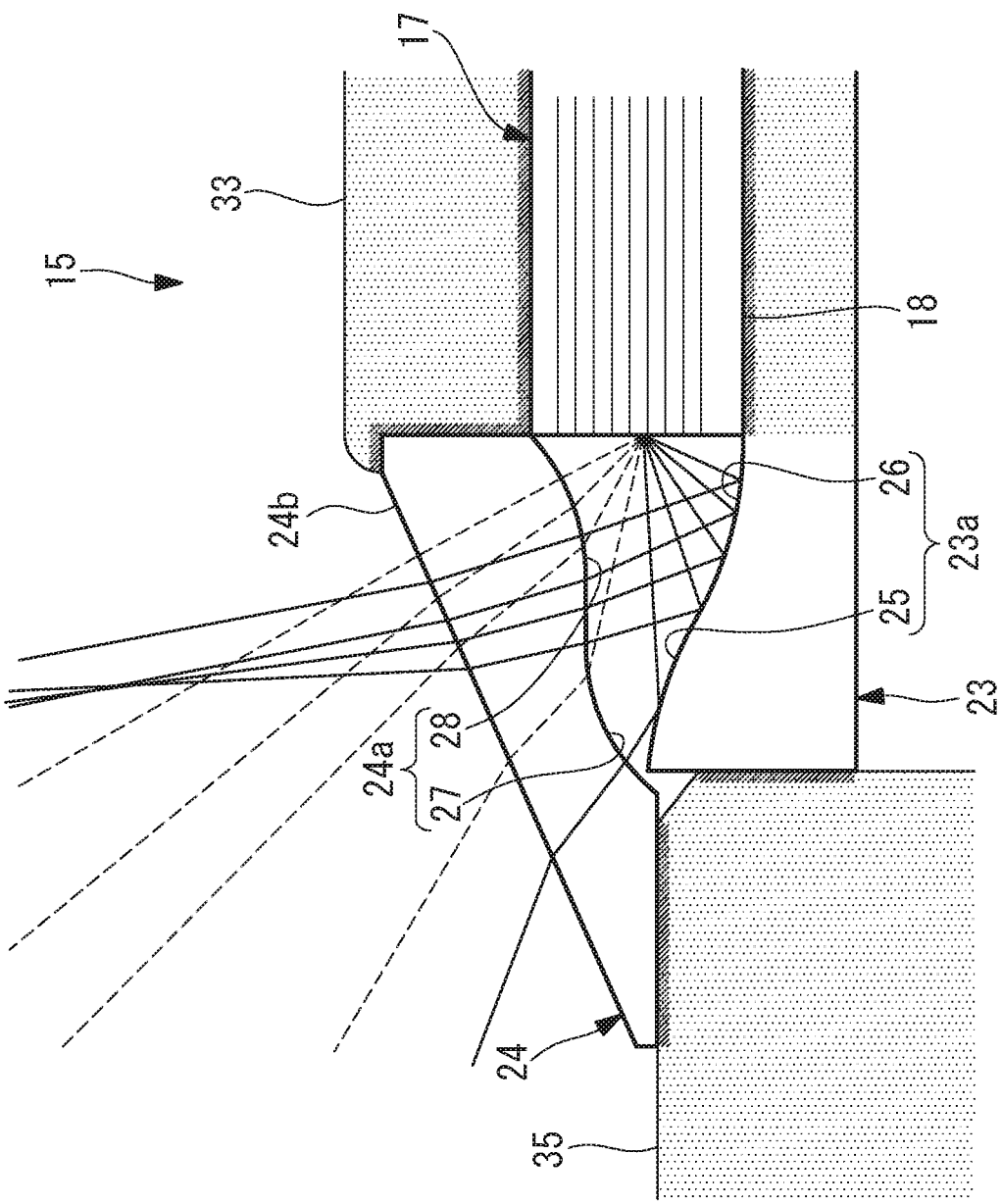
FIG. 13A is a longitudinal sectional view showing an example fixing method of fixing an illumination optical system shown in FIG. 11 to an objective-lens frame.
Figure 13D:
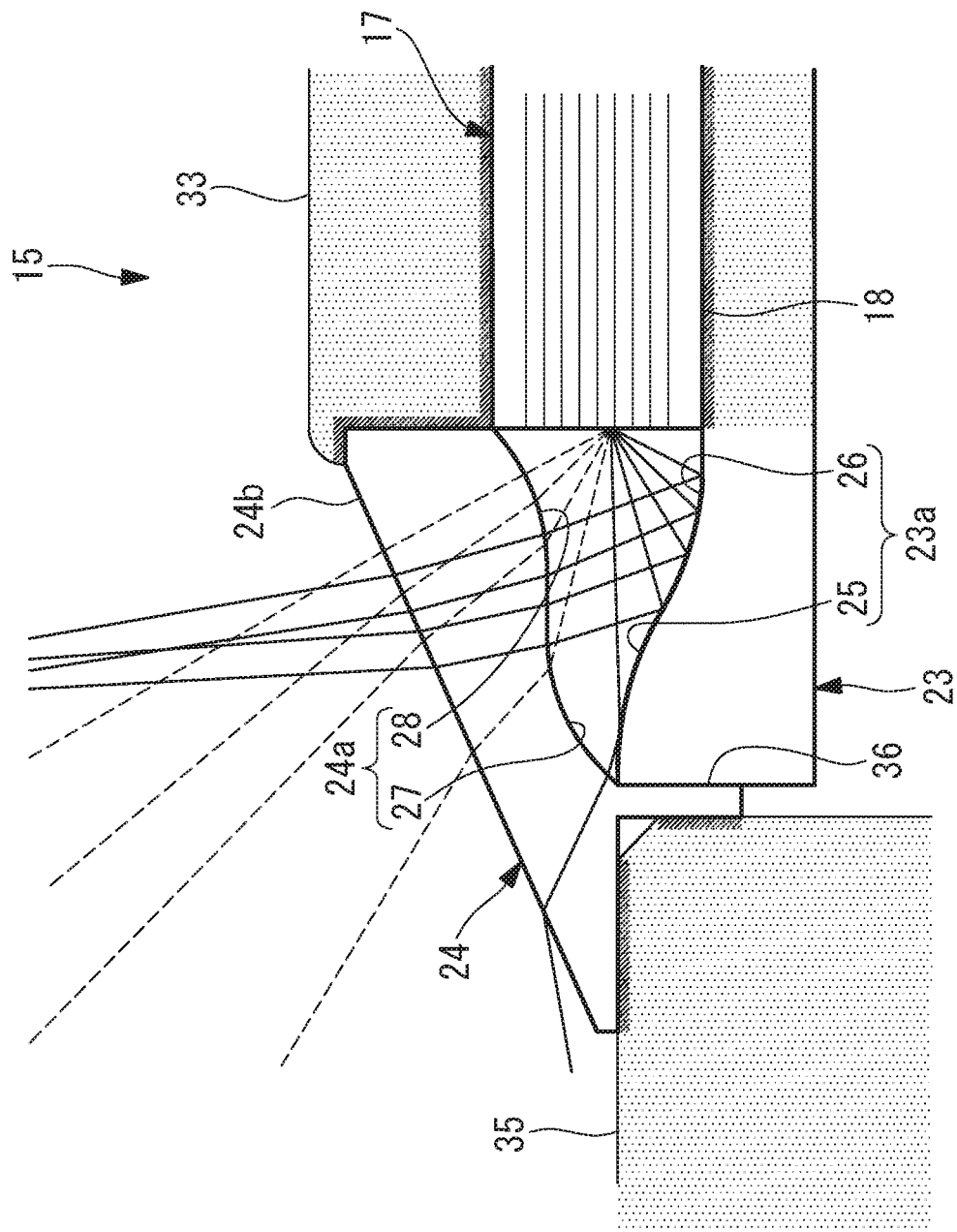
FIG. 13D is a longitudinal sectional view showing an example case in which the first member and the second member of the illumination optical system shown in FIG. 13A can be positioned in the axial direction.

Furthermore, as a method of fixing the illumination optical system 15 to a frame 35 used for the lateral-observation objective lens 8 of the image capturing optical system 14, when a method of separately bonding the first member 23 and the second member 24 to the frame 35 is adopted, as shown in FIG. 13A, it is difficult to position the first member 23 and the second member 24 in the axial direction, as shown in FIGS. 13B and 13C. In such cases, as shown in FIG. 13D, for example, an inner-guard flange section 36 that is made to abut against the frame 35 in the axial direction is provided on the second member 24, and the first member 23 is made to abut against the flange section 36 in the axial direction.

By doing so, the first member 23, the second member 24, and the lateral-observation objective lens 8 can be easily positioned in the axial direction and fixed. Furthermore, in this case, at regions where the first member 23 and the second member 24 are bonded to the lateral-observation objective lens 8, a black adhesive agent or the like may be used, for example, to absorb illumination light. Accordingly, it is possible to prevent illumination light from being directly incident at the lateral-observation objective lens 8.

Figure 14A:
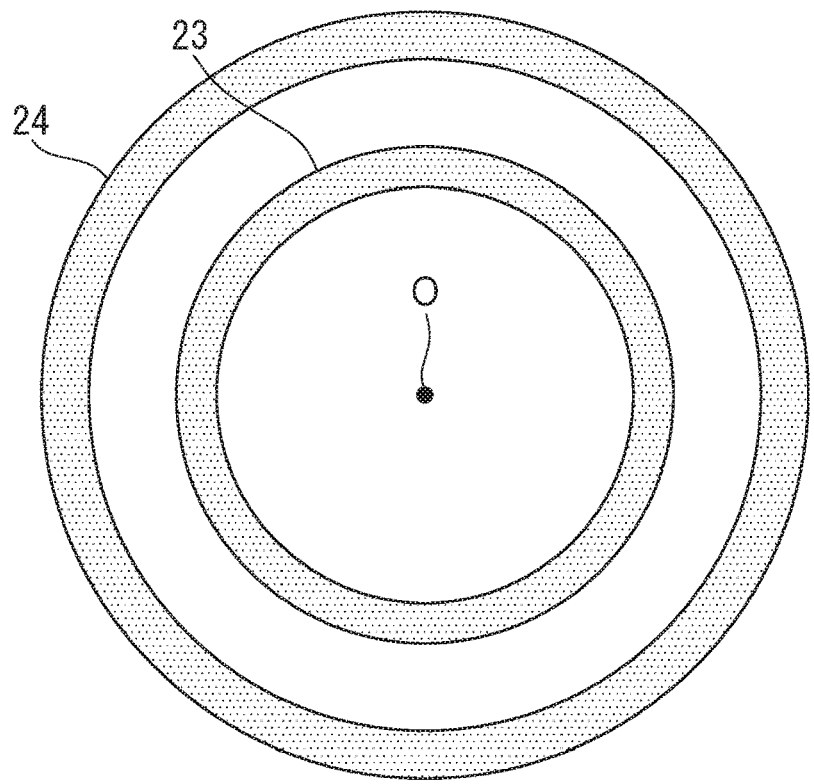
FIG. 14A is a transverse sectional view showing an example of the illumination optical system shown in FIG. 5A.

Furthermore, as shown in FIG. 14A, the first member 23 and the second member 24 of the illumination optical system 15 are each formed into a complete solid of revolution disposed around the optical axis O of the image capturing optical system 14 over the entire circumference, thereby making it possible to uniformly guide illumination light over the entire circumference, which is preferable. However, as shown in FIGS. 2 and 3, in general, the endoscope 1 has a configuration in which the water supply nozzle 13 etc. are disposed on a partial section of the lateral-observation objective lens 8 in the circumferential direction, and, in that case, part of the lateral visual field is missing.

Figure 14B:
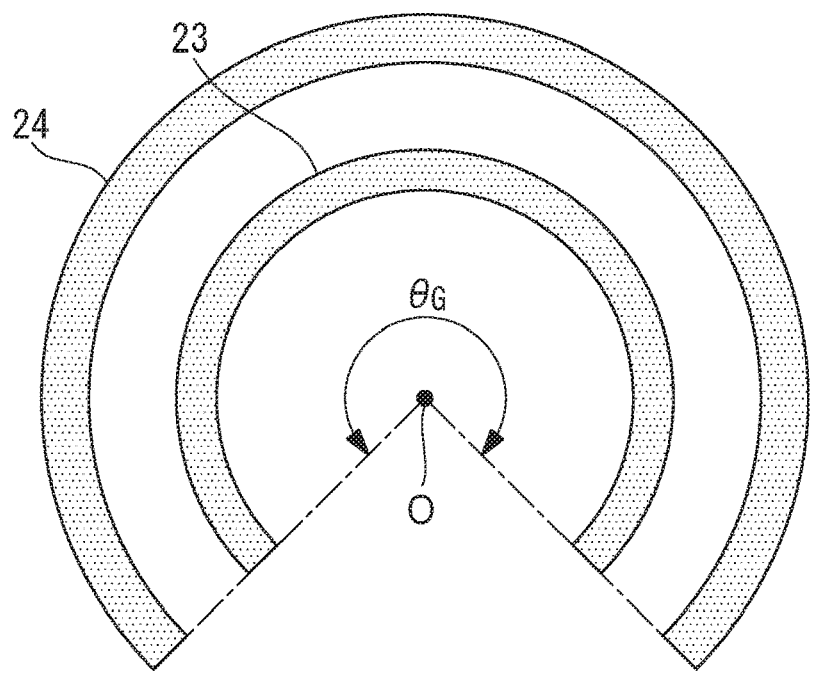
FIG. 14B is a transverse sectional view showing another example of the illumination optical system shown in FIG. 5A.

In this case, as shown in FIG. 14B, it is desired that the illumination optical system 15 be provided within an angular range θG<300° in the circumferential direction. Furthermore, in this embodiment, although a description has been given of a case in which the optical axis O of the image capturing optical system 14 serves as the central axis of the illumination optical system 15, the present invention is not limited thereto, and the optical axis O thereof may be eccentric.

Figure 15:
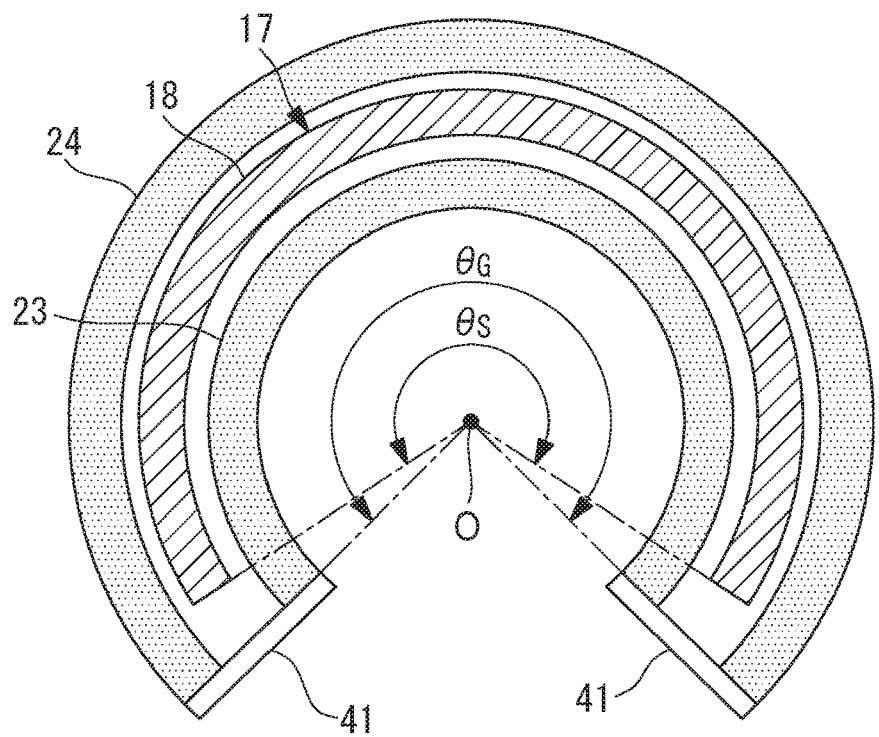
FIG. 15 is a transverse sectional view showing an example of the positional relationship between an illumination optical system shown in FIG. 14B and a light guide.

FIG. 15 shows an example case in which the light guide 17 is arranged in a cylindrical manner in which a partial section thereof in the circumferential direction is notched, with the optical axis O of the image capturing optical system 14 serving as the central axis. In order to efficiently cause illumination light emitted from the emission end of the light guide 17 to be incident at the illumination optical system 15, it is preferred that an angle θS of the light guide 17 in the circumferential direction satisfy the following relationship;

$$\theta S \leq \theta G.$$

Figure 16:
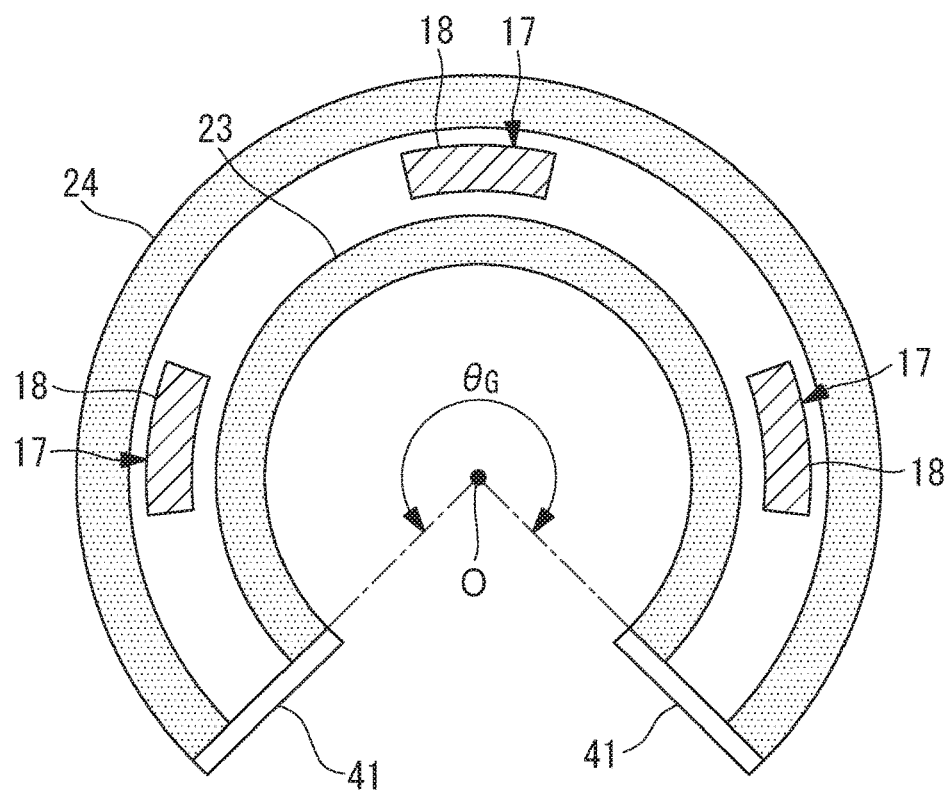
FIG. 16 is a transverse sectional view showing another example of the positional relationship between the illumination optical system shown in FIG. 14B and light guides.
Figure 17:
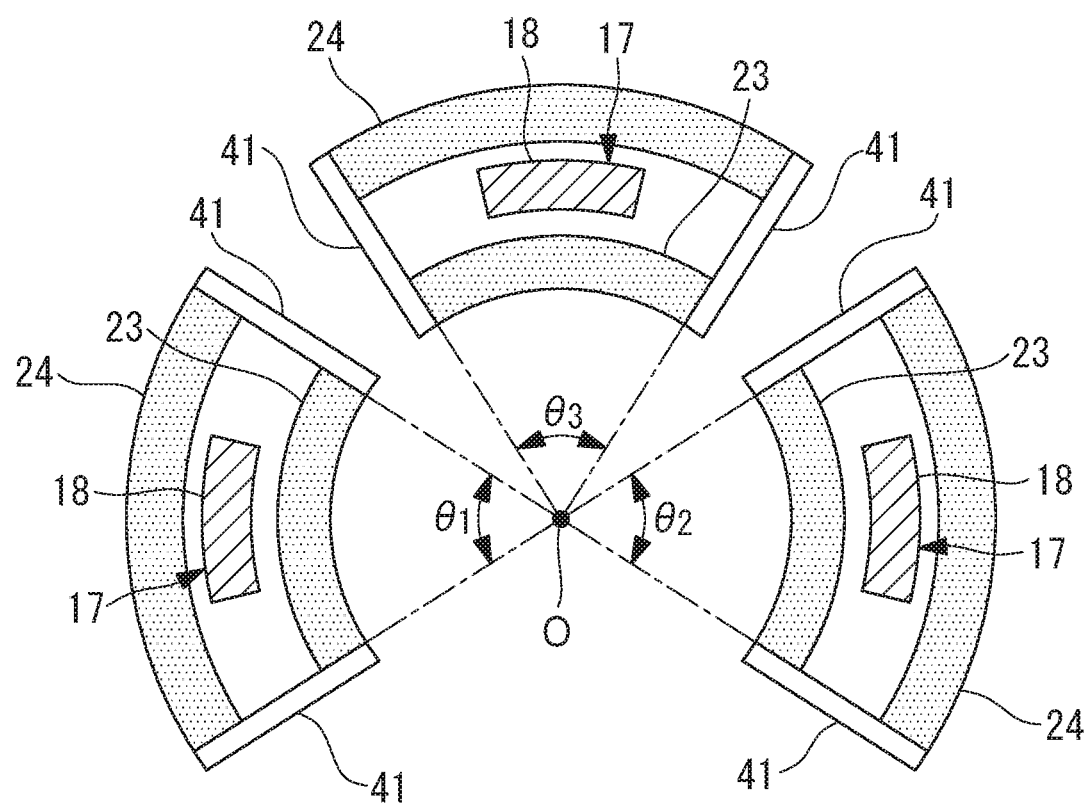
FIG. 17 is a transverse sectional view showing an example case in which an illumination optical system shown in FIG. 16 is divided in the circumferential direction.

Furthermore, as shown in FIGS. 15, 16, and 17, it is also possible to provide second reflective parts 41 on the circumferential end surfaces of the first member 23 and the second member 24 of the illumination optical system 15. By doing so, illumination light is prevented from leaking to an outer side of the illumination optical system 15 without being incident at the reflective surface 23a and the refractive surface 24a, thus making it possible to improve the illumination efficiency.

Instead of the light guide 17 arranged in a cylindrical manner in FIG. 15, it is also possible to dispose a plurality of light guides 17 at intervals in the circumferential direction, as shown in FIG. 16. Unlike the case of FIG. 15, it is not necessary to arrange the light guide 17 in a cylindrical manner.

Furthermore, the first member 23 and the second member 24 of the illumination optical system 15 need not each have the structure of a solid of revolution. Specifically, as shown in FIG. 17, a plurality of pairs consisting of first members 23 and second members 24, each having a circular arc in a transverse section centered on the optical axis O of the image capturing optical system 14, may be disposed at intervals in the circumferential direction. FIG. 17 shows an example case in which three pairs of the first members 23 and the second members 24 are disposed at intervals in the circumferential direction, and the circumferential lengths of the respective pairs of the first members 23 and the second members 24 may be equivalent to or different from each other. FIG. 17 shows the example case in which the angles of the respective first members 23 and second members 24 in the circumferential direction are θ1, θ2, and θ3.

Figure 18:
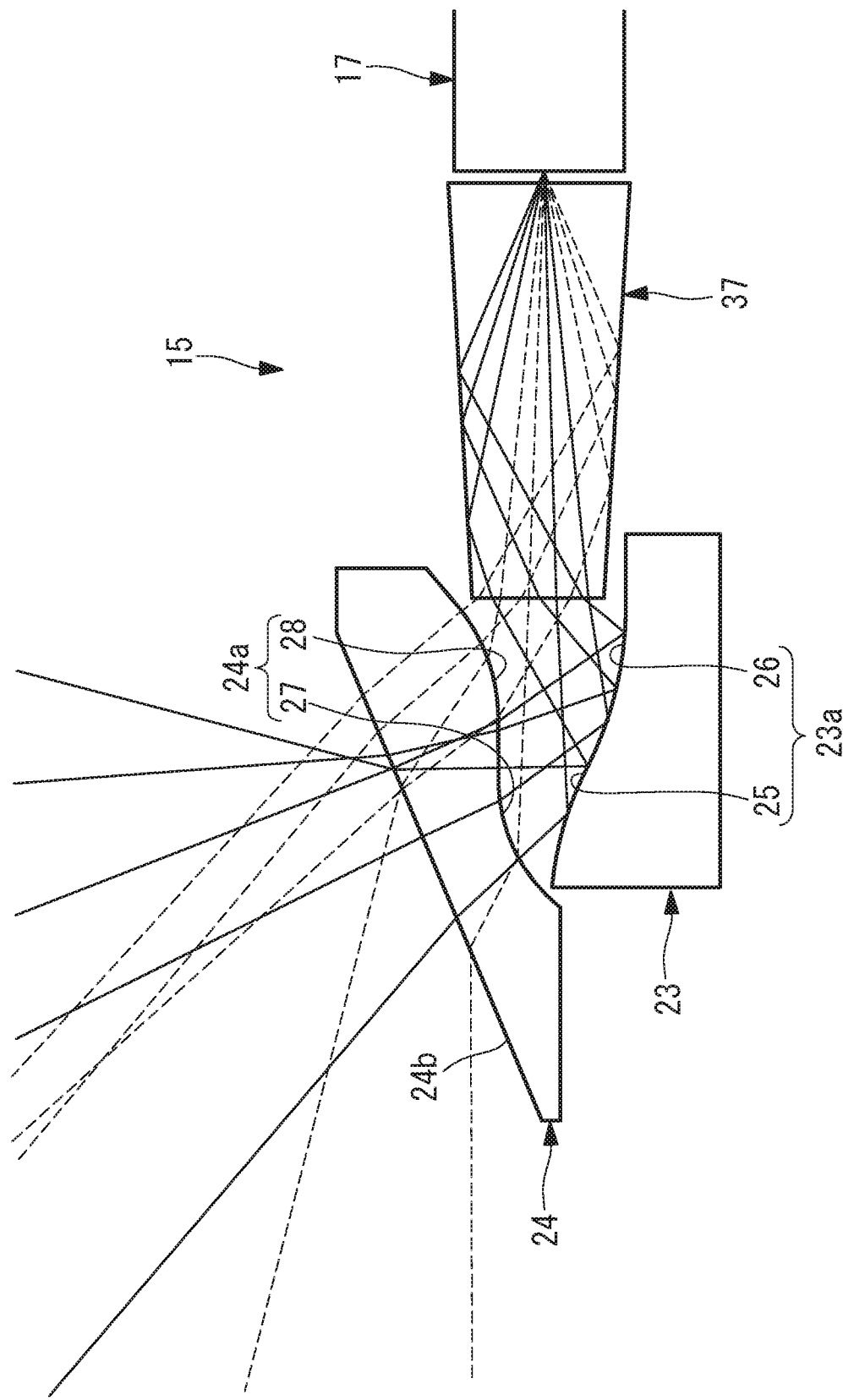
FIG. 18 is a perspective view showing an example case in which a light guiding part is disposed between the illumination optical system shown in FIG. 5A and the light guide.

Furthermore, as shown in FIG. 18, a light guiding part 37 may be disposed between the light guide 17, and the first member 23 and the second member 24, the light guiding part 37 having a longitudinal-sectional tapered shape that is tapered in the traveling direction of illumination light, in a longitudinal section including the optical axis O.

By doing so, while illumination light is being guided in the light guiding part 37, the NA thereof is increased. Therefore, when emitted from an emission end of the light guiding part 37 toward the illumination optical system 15, illumination light having a large NA is emitted, thus making it possible to illuminate a wider range.

Furthermore, because illumination light is subjected to mixing while being guided in the light guiding part 37, it is possible to eliminate unevenness, such as color unevenness. In particular, as in the first member 23 and the second member 24, the light guiding part 37 is formed into a solid-of-revolution obtained by rotation about the optical axis O or is formed to have a structure in which a partial section of the light guiding part 37 in the circumferential direction is notched, thereby guiding illumination light in the light guiding part 37 while causing the illumination light to spread also in the circumferential direction, even though the light guide 17 is not formed into a solid of revolution; thus, it is possible to enhance the mixing effect and to perform uniform illumination.

Figure 19:
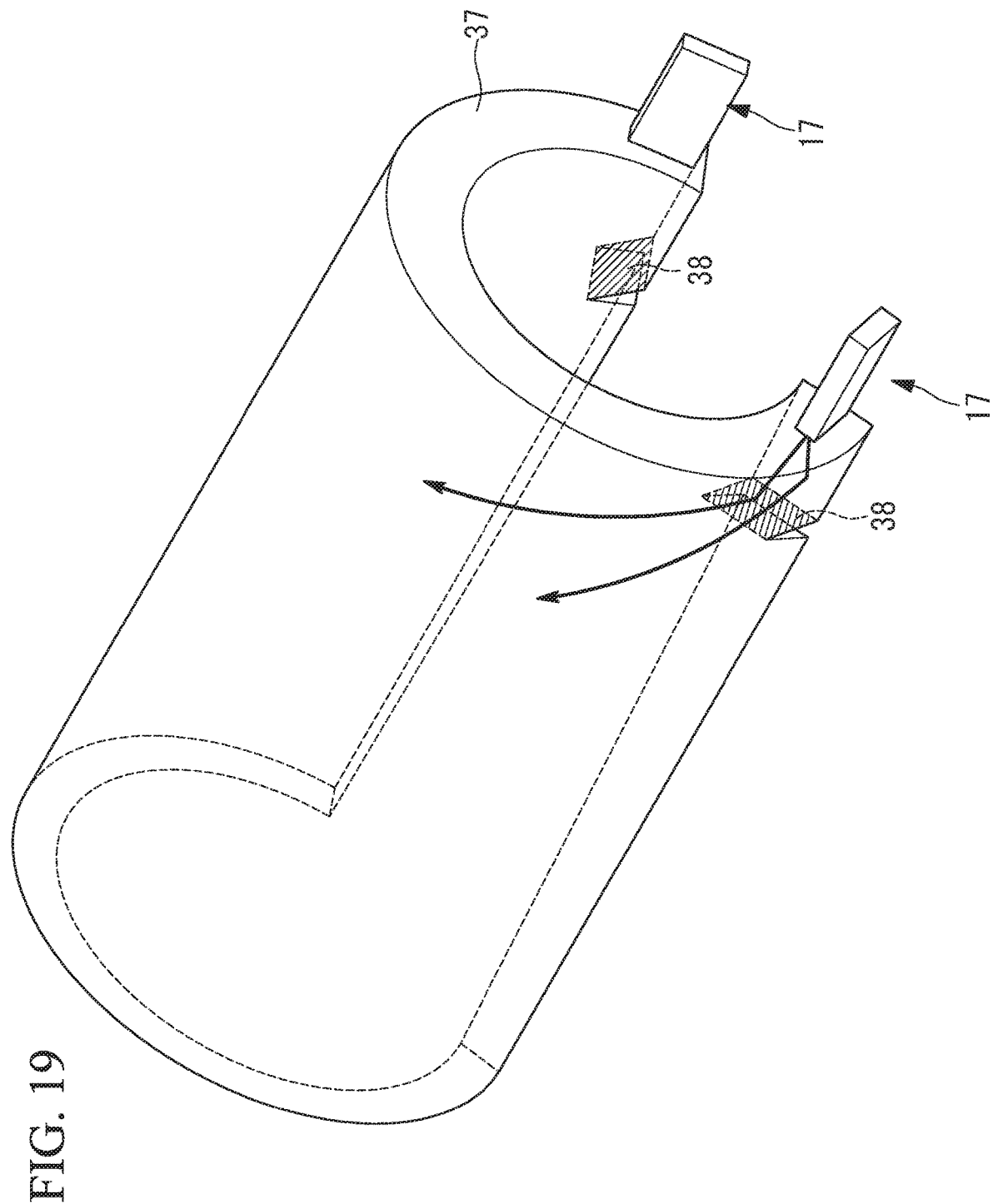
FIG. 19 is a perspective view showing: a light guiding part that is obtained by providing deflection parts on circumferential end surfaces of the light guiding part shown in FIG. 18; and light guides.

Furthermore, as shown in FIG. 19, deflection parts 38 that are formed of inclined surfaces for deflecting, in the circumferential direction, at least part of the illumination light incident from light guides 17 may be provided on circumferential end surfaces of a substantially cylindrical light guiding part 37 that is obtained by notching a partial section of the light guiding part 37 in the circumferential direction. By doing so, the illumination light can be deflected in the circumferential direction of the light guiding part 37 and can be guided in a spiral manner, thus making it possible to generate uniform illumination light. In this case, because there is also an effect of spreading the illumination light in the circumferential direction of the light guiding part 37, this is preferred for a case in which the sizes of the light guides 17 are small with respect to an incident end surface of the light guiding part 37.

Figure 20A:
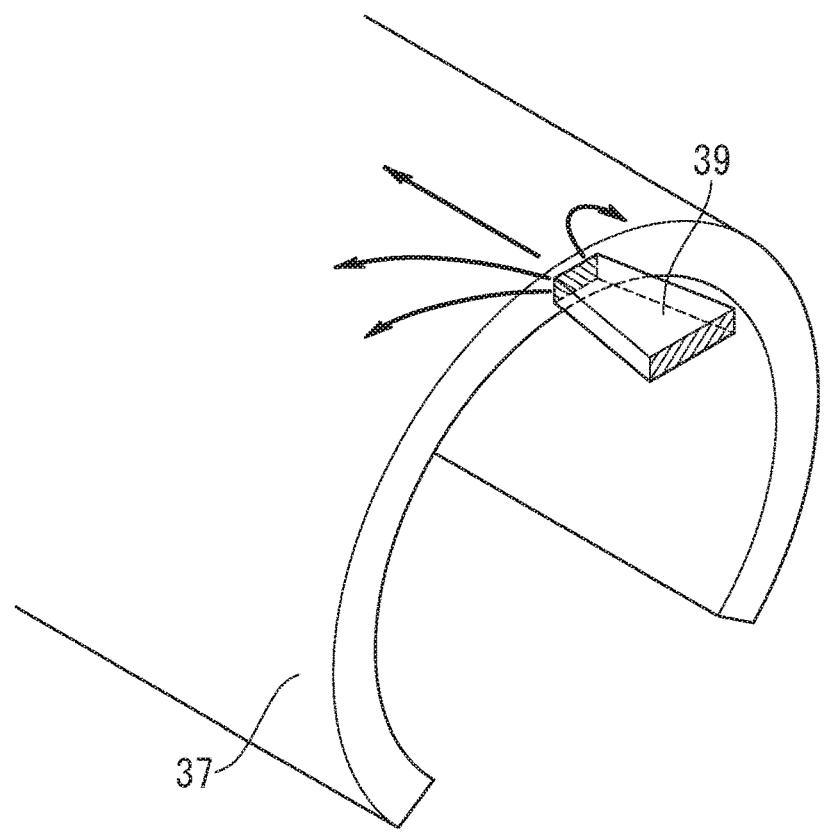
FIG. 20A is a perspective view showing an example case in which a second light guiding part is disposed between the light guiding part shown in FIG. 18 and the light guide.

Furthermore, as shown in FIG. 20A, a second light guiding part 39 may also be disposed between the light guide 17 and the light guiding part 37.

Figure 20B:
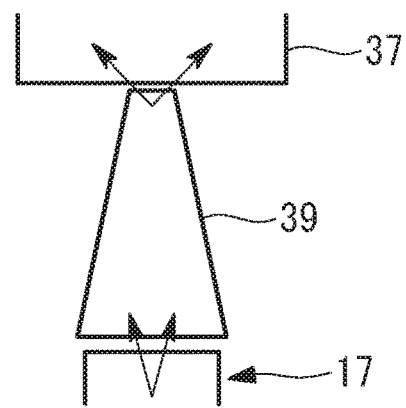
FIG. 20B is a view of the second light guiding part shown in FIG. 20A, viewed from a radial direction.
Figure 20C:
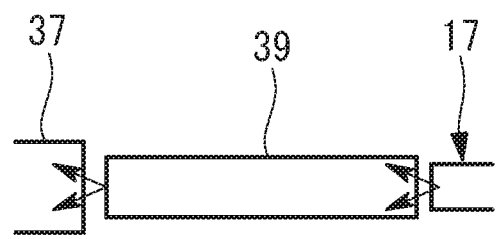
FIG. 20C is a view of the second light guiding part shown in FIG. 20A, viewed from a tangential direction.

FIG. 20A is a perspective view showing the second light guiding part 39 connected to the light guiding part 37 shown in FIG. 18. FIG. 20B is a plan view showing the light guiding part 37 shown in FIG. 18, the second light guiding part 39, and the light guide 17. FIG. 20C is a side view showing the light guiding part 37 shown in FIG. 18, the second light guiding part 39, and the light guide 17.

The second light guiding part 39 has a tapered shape that has an incident surface on which illumination light is incident and an emission surface from which the illumination light is emitted, and the transverse-section area thereof is reduced from the incident surface toward the emission surface. By connecting the second light guiding part 39, which has such a shape, when illumination light is made to enter the light guiding part 37, the illumination light can be spread in the circumferential direction and can be uniformly guided, inside the light guiding part 37, in the circumferential direction.

This structure is also preferred for a case in which the size of the light guide 17 is small with respect to the incident surface of the light guiding part 37.

Furthermore, without using the second light guiding part 39, it is also possible to obtain a similar effect by using the shape of the incident end surface of the light guiding part 37, as shown in FIGS. 21A, 21B, 21C, and 22.

Figure 21A:
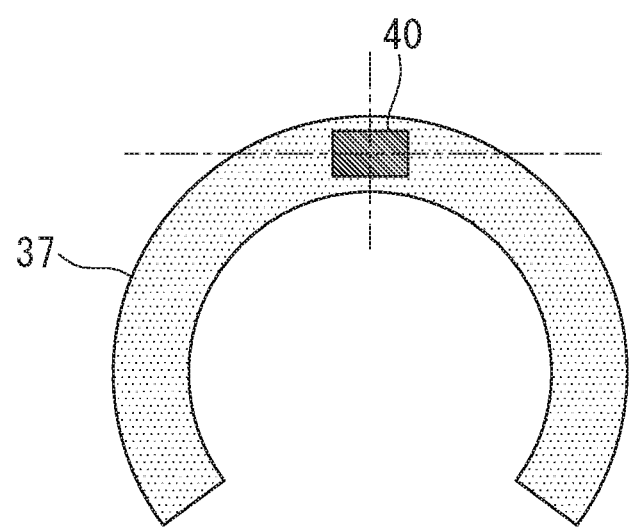
FIG. 21A is a front view for explaining a deflection part that is provided on an incident end surface of the light guiding part shown in FIG. 18.
Figure 21B:
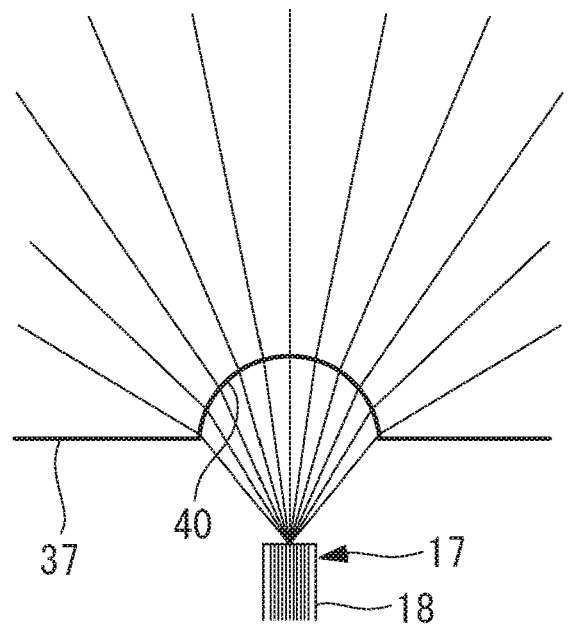
FIG. 21B is a view of the deflection part shown in FIG. 21A, viewed from a radial direction.

Specifically, as shown in FIG. 21B, a deflection part 40 formed of a concave surface that is concave so as to have a semicircular shape in the circumferential direction and so as to have a fixed thickness in radial directions may be formed on at least a partial section of the incident end surface of the light guiding part 37.

Figure 21C:
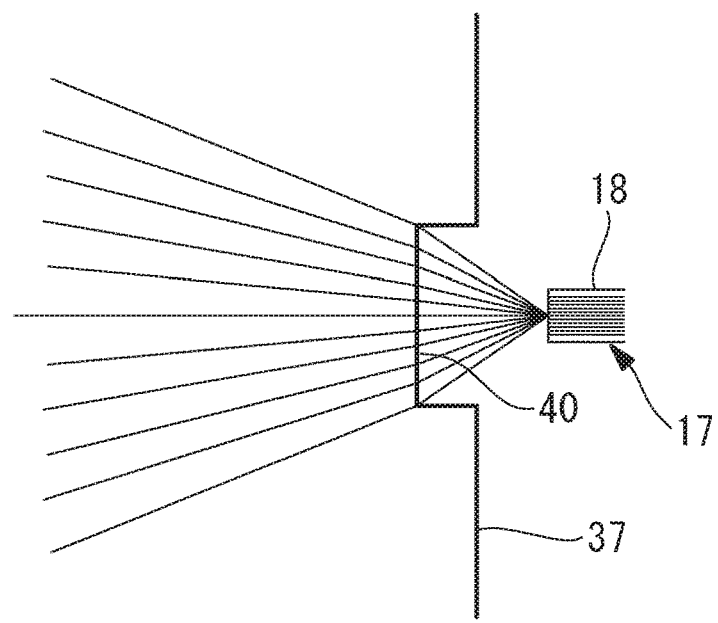
FIG. 21C is a view of the deflection part shown in FIG. 21B, viewed from a tangential direction.
Figure 22:
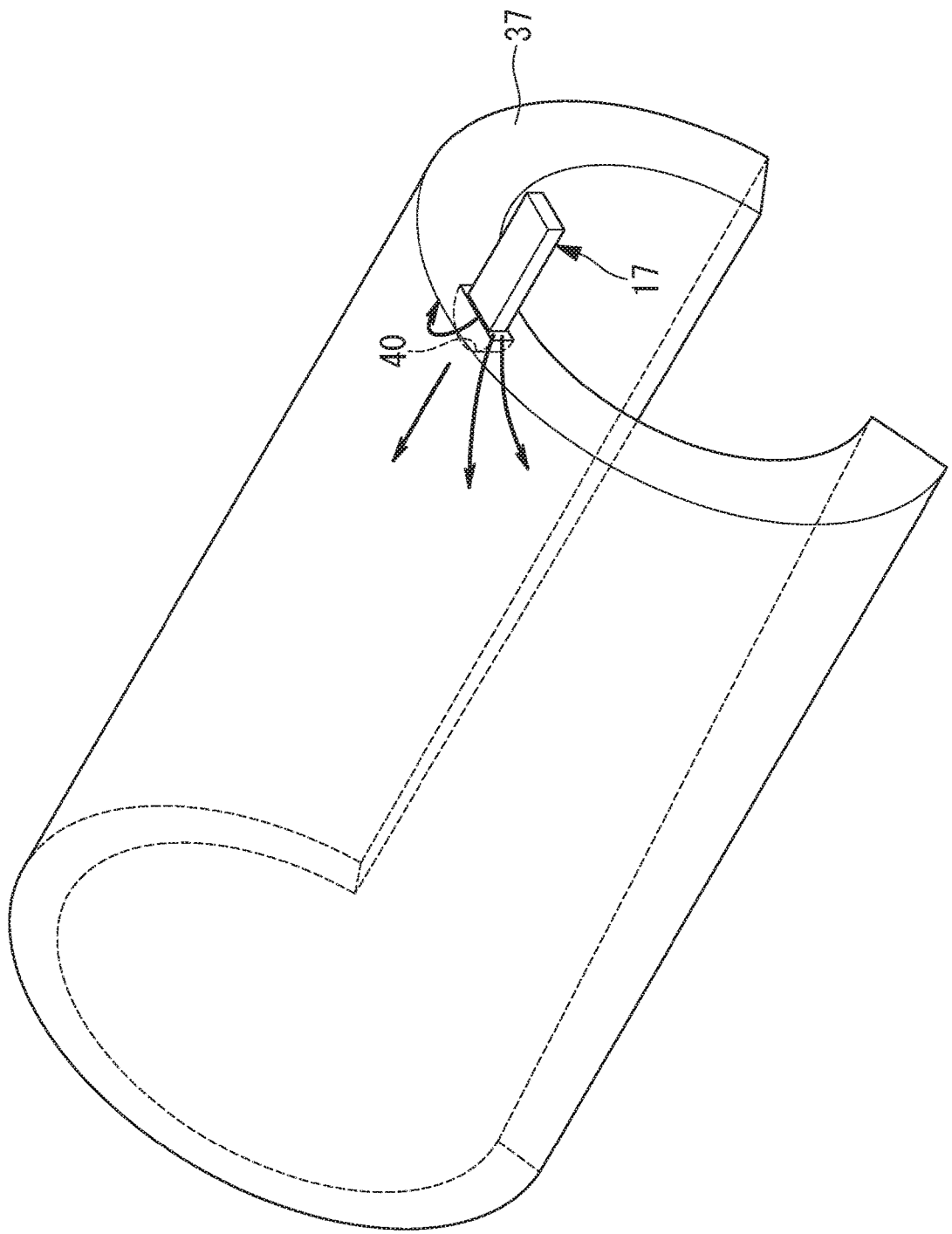
FIG. 22 is a perspective view showing: a light guiding part that has the deflection part shown in FIG. 21A; and the light guide.

The deflection part 40 has an effect of increasing the NA of the illumination light in the circumferential direction, as shown in FIG. 21B, and has an effect of reducing the NA of the illumination light in radial directions, as shown in FIG. 21C. Accordingly, there is an advantage in that the illumination light emitted from the light guide 17 can be spread in the circumferential direction of the light guiding part 37 and can be uniformly guided in the light guiding part 37.

The shape of the deflection part 40 is not limited to a semicircular shape, and it is also possible to adopt a deflection part 40 that has an arbitrary shape, such as a rectangular shape, a triangular shape, a trapezoidal shape, or the like.

Furthermore, although an example case in which the deflection part 40 is provided at one place in the circumferential direction is shown, it is also possible to dispose a plurality of deflection parts 40 at intervals in the circumferential direction.

Furthermore, the reflective surface 23*a* of the illumination optical system 15 and the deflection parts 38, which are shown in FIG. 19, may be coated with metal (for example, aluminum or silver), a dielectric multilayer film, or an oxide multilayer film, to increase the reflectance.

Furthermore, although a description has been given of an example case in which illumination light from the light source device 20 is guided by using the light guide 17, the present invention is not limited thereto, and it is also possible to adopt another light source unit, such as an LED or a laser light source.

The above-described embodiment leads to the following invention.

According to one aspect, the present invention provides an image capturing device including: an image capturing optical system that has an optical axis and that captures an image of surroundings in directions around the optical axis; and at least one illumination optical system that is disposed at a position so as to surround the optical axis of the image capturing optical system, wherein the illumination optical system is provided with: a reflective surface that deflects, through reflection, part of illumination light emitted from an emission end from which the illumination light from a light source unit is emitted; a refractive surface that deflects, through refraction, the other part of the illumination light and the illumination light that has been reflected by the reflective surface; and an emission surface from which the illumination light that has been refracted by the refractive surface is emitted; in a cross section including the optical axis, the reflective surface has an area that is inclined in such a direction as to become farther away from the optical axis toward the front side; the refractive surface has an area that is inclined in such a direction as to approach the optical axis toward a front side and is disposed between the reflective surface and the emission surface; and the emission end is disposed at a radial position between a rear end of the refractive surface and a rear end of the reflective surface.

According to this aspect, when illumination light from the light source unit is emitted from the emission end, part of the illumination light is deflected, through reflection, at the reflective surface, which is provided in the illumination optical system, and the other part of the illumination light and the illumination light that has been reflected by the reflective surface are deflected, through refraction, at the refractive surface and are then emitted from the emission surface to directions around the optical axis of the image capturing optical system. Then, light from an observation target whose image is captured by the image capturing optical system.

The illumination light emitted from the emission end is split into two groups. One of them is deflected, through reflection, at the reflective surface, is then deflected, through refraction, at the refractive surface, and is emitted from the emission surface. The other of them is deflected, through refraction, at the refractive surface without being incident at the reflective surface and is emitted from the emission surface. The illumination light that has been routed via the inclined reflective surface mainly illuminates a lateral area, and the illumination light that has not been routed via the reflective surface mainly illuminates a forward area. Accordingly, illumination for a wide range can be performed. Furthermore, the boundary between illuminated areas illuminated with the two illumination light groups, which are split through refraction at the refractive surface, is eliminated, thus making it possible to perform uniform illumination. Furthermore, because illumination light is refracted by the refractive surface at angles at which total reflection does not occur at the emission surface, it is possible to reduce unnecessary light, such as return light, thus improving the illumination efficiency.

In the above-described aspect, in a cross section including the optical axis, a radial distance between the rear end of the refractive surface and the rear end of the reflective surface may be larger than a radial distance between a front end of the refractive surface and a front end of the reflective surface; and the front ends of the refractive surface and the reflective surface may be disposed at radial positions within a radial range of the emission end.

By doing so, it is possible to eliminate illumination light that is incident at the emission surface without being routed via the reflective surface and the refractive surface, thus improving the illumination efficiency.

Furthermore, in the above-described aspect, a light path between the reflective surface and the refractive surface may be filled with air.

By doing so, refraction at the refractive surface is increased, thus making it easy to eliminate the boundary between lateral and forward illuminated areas and making it possible to perform more uniform illumination. Furthermore, refraction at the refractive surface is increased, thus making it possible to reduce illumination light to be totally reflected at the emission surface and to perform higher-efficiency illumination.

Furthermore, in the above-described aspect, in a cross section including the optical axis, in an area of the reflective surface on which the illumination light is incident, intersection points of at least some of the normals of the reflective surface and an extended line of the emission end may be located at a radially outer side of the emission end.

By doing so, illumination light reflected at the reflective surface is hardly returned to the emission end, thus making it possible to improve the illumination efficiency.

Furthermore, in the above-described aspect, of the illumination light that has been reflected at the reflective surface, the percentage of illumination light that is transmitted through the refractive surface and that is then emitted from the emission surface may be 70% or more.

Furthermore, in the above-described aspect, in a cross section including the optical axis, in 70% or more of the area of the reflective surface on which the illumination light is incident, the intersection points of the normals of the reflective surface and the extended line of the emission end may be located at a radially outer side of the emission end.

By doing so, the illumination efficiency can be improved.

Furthermore, in the above-described aspect, in a cross section including the optical axis, the reflective surface may have a convex section that is convex toward the emission surface.

By doing so, illumination light incident at the reflective surface is spread by being reflected at the convex-shaped reflective surface, is then refracted at the refractive surface and the emission surface, and is emitted to the outside, thereby making it possible to perform wide-range illumination.

Furthermore, in the above-described aspect, in a cross section including the optical axis, the reflective surface may have, at a rear side of the convex section, a concave section that is concave toward the emission surface.

By doing so, it is possible to reduce illumination light returning to the emission end after being reflected at the reflective surface and to improve the illumination efficiency.

Furthermore, in the above-described aspect, in a cross section including the optical axis, the refractive surface may have a bent section.

By doing so, it is possible to achieve expansion of an illuminated area and a reduction in unevenness of the illumination light, due to the lens effect at the refractive surface.

Furthermore, in the above-described aspect, in a cross section including the optical axis, the refractive surface may have a convex section that is convex toward the emission surface and a concave section that is concave toward the emission surface, the concave section being disposed at a rear side of the convex section.

By doing so, a diffusion function and a convergence function are provided due to the convex lens effect and the concave lens effect at the refractive surface, thereby making it possible to achieve expansion of an illuminated area and a reduction in unevenness of the illumination light.

REFERENCE SIGNS LIST 1 image capturing device (endoscope)
14 image capturing optical system
15 illumination optical system
20 light source device (light source unit)
23a reflective surface
24a refractive surface
24b emission surface
25 convex surface section (convex section)
26 concave surface section (concave section)
27 concave surface section (concave section, bent section)
28 convex surface section (convex section, bent section)
O optical axis

The invention claimed is:

1. An image capturing device comprising:
an image capturing optical system that has an optical axis and that captures an image of surroundings in directions around the optical axis; and
at least one illumination optical system that is disposed at a position so as to surround the optical axis of the image capturing optical system,
wherein the illumination optical system is provided with:
a reflective surface that deflects, through reflection, part of illumination light emitted from an emission end from which the illumination light from a light source unit is emitted; a refractive surface that deflects, through refraction, the other part of the illumination light and the illumination light that has been reflected by the reflective surface; and an emission surface from which the illumination light that has been refracted by the refractive surface is emitted;
in a cross section including the optical axis,
the reflective surface has an area that is inclined in such a direction as to become farther away from the optical axis toward the front side;
the refractive surface has an area that is inclined in such a direction as to approach the optical axis toward a front side and is disposed between the reflective surface and the emission surface; and
the emission end is disposed at a radial position between a rear end of the refractive surface and a rear end of the reflective surface.

2. The image capturing device according to claim 1, wherein, in a cross section including the optical axis,
a radial distance between the rear end of the refractive surface and the rear end of the reflective surface is larger than a radial distance between a front end of the refractive surface and a front end of the reflective surface; and the front ends of the refractive surface and the reflective surface are disposed at radial positions within a radial range of the emission end.

3. The image capturing device according to claim 1, wherein a light path between the reflective surface and the refractive surface is filled with air.

4. The image capturing device according to claim 2, wherein, in a cross section including the optical axis, in an area of the reflective surface on which the illumination light is incident, intersection points of at least some of the normals of the reflective surface and an extended line of the emission end are located at a radially outer side of the emission end.

5. The image capturing device according to claim 4, wherein, of the illumination light that has been reflected at the reflective surface, the percentage of illumination light that is transmitted through the refractive surface and that is then emitted from the emission surface is 70% or more.

6. The image capturing device according to claim 4, wherein, in a cross section including the optical axis, in 70% or more of the area of the reflective surface on which the illumination light is incident, the intersection points of the normals of the reflective surface and the extended line of the emission end are located at a radially outer side of the emission end.

7. The image capturing device according to claim 1, wherein, in a cross section including the optical axis, the reflective surface has a convex section that is convex toward the emission surface.

8. The image capturing device according to claim 7, wherein, in a cross section including the optical axis, the reflective surface has, at a rear side of the convex section, a concave section that is concave toward the emission surface.

9. The image capturing device according to claim 7, wherein, in a cross section including the optical axis, the refractive surface has a bent section.

10. The image capturing device according to claim 7, wherein, in a cross section including the optical axis, the refractive surface has a convex section that is convex toward the emission surface and a concave section that is concave toward the emission surface, the concave section being disposed at a rear side of the convex section.

* * * * *